(12) United States Patent
Shin

(10) Patent No.: US 12,414,933 B2
(45) Date of Patent: Sep. 16, 2025

(54) POLYPHOSPHAZENE DRUG CARRIERS

(71) Applicant: ONSELEX PHARMACEUTICALS, INC., New York, NY (US)

(72) Inventor: Ernest E. Shin, New York, NY (US)

(73) Assignee: ONSELEX PHARMACEUTICALS, INC.

( * ) Notice: Subject to any disclaimer, the term of this patent is extended or adjusted under 35 U.S.C. 154(b) by 543 days.

(21) Appl. No.: 17/782,480

(22) PCT Filed: Dec. 2, 2020

(86) PCT No.: PCT/US2020/062945
§ 371 (c)(1),
(2) Date: Jun. 3, 2022

(87) PCT Pub. No.: WO2021/113403
PCT Pub. Date: Jun. 10, 2021

(65) Prior Publication Data
US 2023/0105243 A1    Apr. 6, 2023

Related U.S. Application Data

(60) Provisional application No. 62/942,978, filed on Dec. 3, 2019.

(51) Int. Cl.
*A61K 9/00* (2006.01)
*A61K 9/51* (2006.01)
*A61K 31/337* (2006.01)

(52) U.S. Cl.
CPC .......... *A61K 31/337* (2013.01); *A61K 9/5146* (2013.01)

(58) Field of Classification Search
CPC .................................................. A61K 9/5146
See application file for complete search history.

(56) References Cited

U.S. PATENT DOCUMENTS

2004/0198638 A1   10/2004   Li et al.
2007/0292384 A1   12/2007   Sohn et al.
2009/0047348 A1    2/2009   Song et al.
2009/0181088 A1    7/2009   Song et al.
(Continued)

FOREIGN PATENT DOCUMENTS

CN    106459420 A    2/2017
JP    2009-531471 A  9/2009
JP    2009-532554 A  9/2009
(Continued)

OTHER PUBLICATIONS

Examination Report issued for AU patent application Serial No. 2020396953, dated Jul. 11, 2024.
(Continued)

*Primary Examiner* — Paul W Dickinson
(74) *Attorney, Agent, or Firm* — Westman, Champlin & Koehler, P.A.; Amanda M. Prose

(57) ABSTRACT

The present invention relates generally to hybrid polymer (e.g., polyphosphazene) based drug delivery platforms and to methods of producing, evaluating, administering, and treating subjects with the same. More particularly, the present invention provides polyphosphazene based drug delivery platforms comprising one or more polyphosphazenes with controlled molecular weights and/or polydispersities as well as selective methods for associating one or more therapeutic drug (or prodrug) substances to the polyphosphazenes.

7 Claims, 2 Drawing Sheets

(56) References Cited

U.S. PATENT DOCUMENTS

2016/0367481 A1   12/2016   Zale et al.
2018/0221509 A1    8/2018   Mayer et al.

FOREIGN PATENT DOCUMENTS

| JP | 2017-512888 A | 5/2017 |
| KR | 10-2015-0107650 A | 9/2015 |
| WO | 2007/083875 A2 | 7/2007 |
| WO | 2007/114549 A1 | 10/2007 |
| WO | 2015137777 A1 | 9/2015 |
| WO | 2021/113403 A1 | 6/2021 |

OTHER PUBLICATIONS

International Search Report and Written Opinion issued for PCT/US2020/062945, dated Mar. 25, 2021.
Chun, C., et al. "Thermosensitive poly (organophosphazene)-paclitaxel conjugate gels for antitumor applications" (2009) Biomaterials, 30(12), 2349-2360.
Office Action issued for Chinese patent application Serial No. 202080092638.6, dated Apr. 22, 2023, with English translation.
Office Action issued for Japanese patent application Serial No. 2022-533384, dated Jul. 11, 2023, with English translation.
Allcock, H. R. et al. ""Living" Cationic Polymerization of Phosphoranimines as an Ambient Temperature Route to Polyphosphazenes with Controlled Molecular Weights" Macromolecules (1996) 29, 7740-7747.
Extended European Search Report issued for EP patent application serial No. 20896616.8 dated Oct. 23, 2023.

Polyphosphazene-Paclitaxel Conjugate (PPC)

POLYPHOSPHAZENE DRUG CARRIERS

CROSS-REFERENCE TO RELATED APPLICATION

This Application is a Section 371 National Stage Application of International Application No. PCT/US2020/062945, filed Dec. 2, 2020 and published as WO 2021/113403 A1 on Jun. 10, 2021, in English, which claims priority to U.S. provisional patent application Ser. No. 62/942,978, filed Dec. 3, 2019, the contents of which are hereby incorporated by reference in their entirety.

FIELD OF THE INVENTION

The present invention relates generally to hybrid polymer (e.g., polyphosphazene) based drug delivery platforms and to methods of producing, evaluating, administering, and treating subjects with the same. More particularly, the present invention provides polyphosphazene based drug delivery platforms comprising one or more polyphosphazenes with controlled molecular weights and/or polydispersities as well as selective methods for associating one or more therapeutic drug (or prodrug) substances to the polyphosphazenes.

BACKGROUND OF THE INVENTION

Polyphosphazenes are a broad and well known class of macromolecules based on the repeating unit $—(NPR_2)—_n$, wherein R can be selected from a wide range of organic or inorganic substituent groups. It has been estimated that by mid-1997 roughly 700 types of polyphosphazenes had been synthesized and characterized, approximately 2000 publications and patents had appeared, and disclosures were appearing at a rate of 170-200 per year on this class of polymers. (See, Polyphosphazenes, J. of Inorganic and Organometallic Polymers, 1992, 2(2), 197-211).

The predominant route to polyphosphazenes to date has been through the thermal polymerization of hexachlorocyclotriphosphazene (cyclic trimer), also referred to as phosphonitrilic chloride, to poly(dichlorophosphazene) (which has an IUPAC name of poly(nitrilodichlorophosphoranetriyl). This route is illustrated in Scheme 1 below.

Scheme 1
Polymerization of Hexachlorocyclotriphosphazene

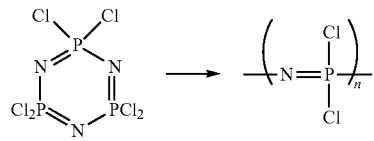

Although poly(dichlorophosphazene) is a hydrolytically unstable elastomer, it can be converted to a wide range of derivatives by macromolecular nucleophilic substitution reactions with a broad variety of nucleophiles. As illustrated in Scheme 2 below, poly(organophosphazenes) are generally prepared by reacting one or more organic or organometallic nucleophiles (R in Scheme 2) with poly(dichlorophosphazene). (See e.g., Allcock et al., Macromol 1986, 19, 1508, and Blonsky et al., J. Am. Chem. Soc. 1984, 106, 6854).

Scheme 2
Synthesis of Poly(organophosphazenes)

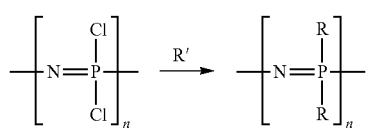

The substituent groups on the polymer backbone largely determine the properties of the resulting polymers. By appropriate selection of the substituent groups, one can obtain a phosphazene polymer with, for example, a target glass transition temperature; target physical characteristics such as film forming properties; organogel or hydrogel behavior; desired hydrophobicity or hydrophilicity; amorphous or microcrystalline character; and advanced liquid crystalline, photochromic, or nonlinear optical properties. (Mark; J. E.; Allcock, H. R.; West, R. Inorganic Polymers Prentice Hall: Englewood Cliffs, N.J. 1992 Chapter 3).

Yet another synthetic route for the production of polyphosphazenes is the Neilson-Wisian-Neilson reaction shown below. (See, Nelson et al., Chem. Rev. 1988, 88, 541).

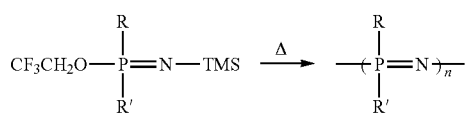

The disadvantages of the Neilson-Wisian-Neilson route include high polymerization temperature, difficult monomer synthesis, the ability to prepare only a limited number of polymers, and little molecular weight control.

The Flindt-Rose Matyjaszewski route for the production of polyphosphazenes involves the following reaction. (See, Makromol. Chem. Macromol. Symp. 1992, 54155, 13).

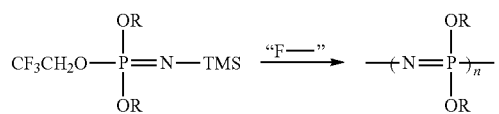

The polymerization temperature of this reaction can be as low as 90° C. The reaction produces polymers with fairly narrow polydispersities (<1.4). The reaction, however, cannot be used to prepare the important synthetic tool poly (dichlorophosphazene). Block copolymers of the type [NP $(OR_1)_2]_x[NP(OR_1)(OR_2)]_y$, wherein $R_1$ is halogenated alkoxy and $R_2$ is an aliphatic or aryl moiety, can be prepared using this reaction. The synthesis of the monomers necessary for this reaction can be difficult.

In still yet another synthetic approach to polyphosphazenes synthesis, the Hombacker and Li reaction provides the following scheme.

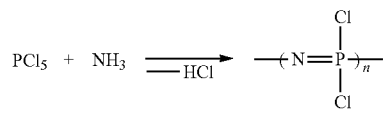

The Hombacker and Li method, however, requires high temperatures and does not provide control over molecular weight. The products do not have narrow polydispersities.

The DeJaeger synthesis provides poly(dichlorophosphazenes) using the following protocol.

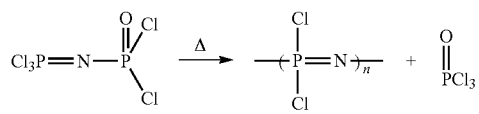

The DeJaeger allows for some molecular weight control, but fails produce polymers with narrow polydispersities. Additionally, this route requires high reaction temperatures and the compound $POCl_3$ is very corrosive.

Azide precursors have also been used to prepare polyphosphazenes. For example, $R_2PCl+NaN_3$ yields $-(N=PR_2)_n$. This route is potentially dangerous however because azides are explosive and toxic. Furthermore this method fails to control molecular weight and cannot produce poly(dichlorophosphazene).

Thus, many of the existing routes for the preparation of polyphosphazenes have one or more disadvantages, including, complicated monomer synthesis, difficult polymer synthesis, or elevated polymerization temperatures that allow only limited ranges of polymers to be produced. It is also difficult using many of these methods to prepare or control the molecular weight and polydispersity of the important polymer, poly(dichlorophosphazene).

Polydispersity is a measure of the molecular weight nonhomogeneity of a polymer sample. Polydispersity is calculated by dividing the weight average molecular weight ($M_w$) of the polymer by the number average molecular weight (Mn). The value of $M_w/M_n$ is unity for a perfectly monodisperse polymer. The thermal polymerization of hexachlorocyclotriphosphazene, for example; results in a molecular weight of $10^5$-$10^6$ or greater. The polydispersity Index (PDI) for these polymers is typically 2 or higher.

It is known that polymers with narrow polydispersity are easier to crystallize, have a sharper glass transition temperature, and flow more suddenly at a given temperature than the same polymer with a broader polydispersity. The polydispersity of polymers used for drug delivery affects the hydrolytic degradation and release properties of the delivery device. For this reason, the U.S. Food and Drug Administration requires that polymers for medical applications such as drug delivery have a very narrow polydispersity.

The absolute molecular weight, as opposed to the range of molecular weight, of a polymer sample is also of prime importance in its behavior in industrial and medical applications. Most important mechanical properties vary considerably with weight average molecular weight. For example, strength increases rapidly with increasing molecular weight until a critical point is reached. The ability to process polymers into useful articles such as film, sheet, pipe, or fiber also increases as molecular weight increases to a point, and then decreases past a point as the viscosity becomes too high. Thus it is often desirable to obtain a high but specified, compromise molecular weight that optimizes strength and processability in a concerted fashion. This illustrates the need to control molecular weight during polymer synthesis such that well characterized and efficiently produced polymers (e.g., polyphosphazenes) with low (or narrow) polydispersity and controlled molecular weights suitable for subsequent development as use as drug delivery platforms result.

Polymers, such as polyphosphazenes with controlled molecular weights and/or polydispersities, are contemplated as providing useful drug platforms provided successful schemes for attaching one or more drug substances of interest can be developed.

Various polymers, including but not limited to, polyphosphazenes, have shown promise as drug delivery vehicles. Nevertheless, wide scale adoption of the of polymeric drug delivery systems has yet to be achieved due shortcomings in the polymers, or in the resultant drug delivery systems, related to, but not limited to, less than suitable biocompatibility, biodegradability, and insufficient hydrophilicity, or alternatively, hydrophobicity.

Therefore, what is needed are processes for the production of polymers, and in particular, polyphosphazenes, and even more particularly, poly(dichlorophosphazene) (e.g., polyphosphazenes and polyphosphazene block copolymers and/or triarmed star polyphosphazenes) that provide polymer products having narrow polydispersity and/or molecular weights that can be subsequently derivitized and used carriers of one or drug substances of interest in relevant patient populations.

BRIEF DESCRIPTION OF THE DRAWINGS

In the drawings, some embodiments are illustrated by way of example, and not limitation, in the figures of the accompanying drawings in which.

SUMMARY OF THE INVENTION

Figure 1:
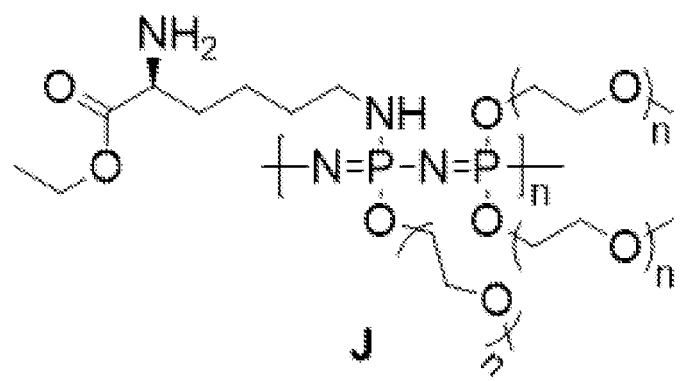
FIG. 1 shows a polyphosphazene produced by the scheme described in Example 14.
Figure 2:
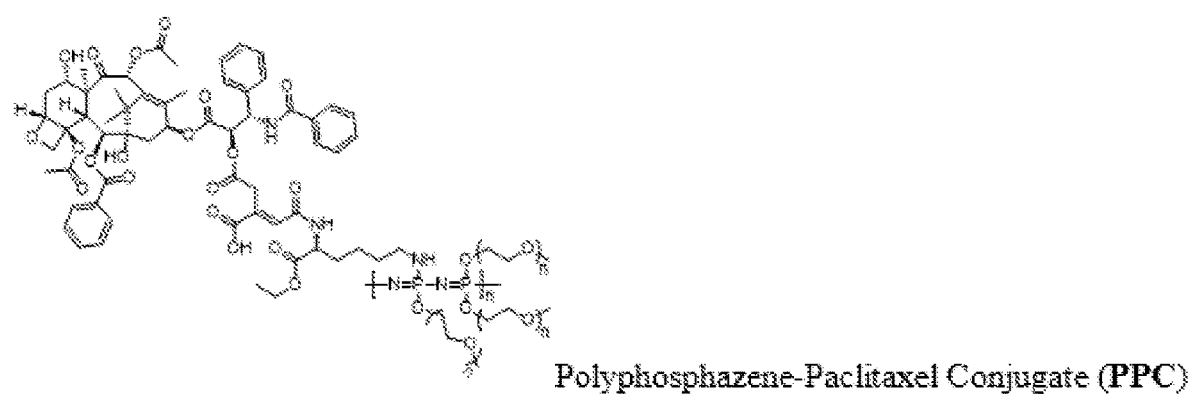
FIG. 2 shows an exemplary polyphosphazene Paclitaxel conjugate contemplated in an embodiment of the present invention.

This invention is in the area of polymer synthesis and drug delivery system production, and in particular, provided herein are convenient and mild processes for preparing hybrid polymers (e.g., polyphosphazenes) having controlled molecular weight and polydispersity. The invention also provides convenient routes for the preparation of monomer, cyclic trimer, triarmed star-polyphosphazene, and block copolymers of these polyphosphazenes.

The polyphosphazenes of the present invention, upon association (e.g., attachment thereto) of one or more active drug substances (or prodrug substances) are useful delivery platforms and carriers for administering compounds of interest to a subject. In various embodiments, the drug substances are typically intended to provide a therapeutic benefit to the subject.

Thus, in certain preferred embodiments, the present invention relates to polyphosphazene based drug delivery platforms and to methods of producing, evaluating, administering, and treating subjects with the same. More particularly, the present invention provides polyphosphazene based drug delivery platforms comprising one or more polyphosphazenes with controlled molecular weights and/or polydispersities as well as selective methods for associating one or more drug substances to the polyphosphazenes.

Further provided are processes for preparing polyphosphazenes that include a cationic solution polymerization reaction of a phosphoranimine, using a main group or transition metal halide, or other appropriate halide salt, including a linear phosphazene salt of any chain length, or a preformed non-phosphazene polymer containing a main or transition metal chloride, as an initiator. In certain preferred embodiments, triarmed-star polyphosphazenes having the formula $N\{RN(H)R'_2P-(N=PR'_2)_n\}_3$ are prepared via this method. Also, provided are methods for synthesis of the monomer $Cl_3P{=}NSiMe_3$ and cyclic trimer $N_3P_3X_6$ from the reactants $N(SiR_3)_3$ and $PX_5$.

In preferred embodiments, the drug delivery platforms are polymer compounds that are substantially biocompatible, biodegradable, and hydrophilic, or alternatively, substantially hydrophobic. In particularly preferred embodiments, the drug delivery platforms comprise polymer compounds comprising hybrid polymers having a main chain containing nitrogen and phosphorous linked through a plurality of interchangeable single and double bonds and optionally further comprising one or more types of advantageous side-chains. Suitable hybrid polymers compounds are preferentially, though not exclusively, found in the broad class of polyphosphazenes compounds formulated as nanospheres, microspheres, micelles, films, or hydrogels. The polyphosphazenes compounds of the present invention are subsequently, or concomitant with production, derivitized (e.g., loaded) with one or more active drug substances (or prodrug) substances. Suitable drug substances include, but are not limited to, one or more anticancer agent (e.g., chemotherapeutic agent(s), hormone therapies, targeted cancer drugs and bisphosphonates, anticancer and/or anti-tumorigenic agents, anti-proliferative agents, antiangiogenic agents, anti-metastatic agents, neoadjuvant therapies and agents, immunological therapies (e.g., "checkpoint inhibitor" agents)).

In still embodiments, suitable hybrid polymers compounds are preferentially, though not exclusively, found in the broad class of methoxy poly(ethylene glycol)-block-poly (ε-caprolactone) ("mPEG-b-PCL or "mPEG-PCL") compounds that are subsequently derivatized with one or more active drug substances (or prodrug) substances, such as one or more anticancer agents or drugs.

In preferred embodiments, the concentration, loading characteristics, adsorption, absorption, or otherwise the chemical association (e.g., covalent, ionic bonding and the like) of the agent(s) to the drug carrier is analyzed by 1H NMR, HPLC, GC, MS, GC-MS, immunological techniques.

Preferred drug loading ratios of therapeutic agent (e.g., chemotherapeutic agent) to drug carrier is from about % to about 20%, and more preferably, from about 5% to about 10% drug/copolymer ratio (w/w). In certain preferred embodiments, the chemotherapeutic agent comprises Paclitaxel loaded in the drug delivery compositions at typical therapeutically proven levels of from 135-175 mg/m$^2$ (i.e., related to ovarian carcinoma studies). In other embodiments, the level of Paclitaxel is from x2, x3, x4, and potentially x5 the typical therapeutic level for the indication. While the present invention is not limited to any particular mechanisms, it is contemplated that increased administrable levels of chemotherapeutic agent(s) (e.g., Paclitaxel) are possible with a number of therapeutic and chemotherapeutic agents when using methods of comprising the drug delivery systems of the present invention.

Aqueous solubility in preferred compositions ranges is from about 1 to 10%, is from about 1% to about 6%, and more preferably is from about 3% to about 4%.

In another embodiment, one or more targeting moieties (e.g., folic acid, sugars, and antibodies, and the like) can be conjugated to chemical active moieties or functional groups on the drug carrier(s) such as pendant functional groups. For example, at least one targeting moiety may be conjugated to a pendant functional group(s) wherein, said targeting moiety is selected from the group comprising vitamins, sugars, lectins, antibodies and antibody fragments, peptides, receptors, ligands, and combinations thereof. In other embodiments, the compositions provide one or more targeting comprising folic acid, sugars, and antibodies, and the like.

In preferred embodiments, the drug delivery systems when loaded with one or more drugs or therapeutic agents are optionally freeze dried and/or lyophilized. In some of the embodiments, one or more cryoprotectants are optionally added to the freeze dried and/or lyophilized. Suitable cryoprotectants include, but are not limited to, polysaccharides (sugars and sugar alcohols) (e.g., Arabinose, Ribose, Ribulose, Xylose, Xylulose, Lyxose, Allose, Altrose, Fructose, Galactose, Glucose, Gulose, Idose, Mannose, Sorbose, Talose, Tagatose, Sedoheptulose, Mannoheptulose, Sucrose, Maltose, Trehalose, Lactose, Mellibiose, Amylaose, and Mannan and the like). (See e.g., Lee, M. K., "Cryoprotectants for freeze drying of drug nano-suspensions: effect of freezing rate," J. Pharm. Sci., 98(12) pp. 4808-4817, 2009). The present invention contemplates, the use of one or more sugar cryoprotectants, and more preferably, the use of sucrose, to stabilize the drug delivery systems during freeze drying and/or lyophilization processing. Percentages of the cryoprotectants in particular drug delivery systems range from about 0.001% to about 10% or more, from about 0.01% to about 10% or more, from about 0.1% to about 10% or more, from about 0.001% to about 5% or more, from about 0.01% to about 5% or more, from about 0.1% to about 5% or more, from about 0.5% to about 5% or more, from about 0.5% to about 10% or more, from about 1% to about 10% or more, from about 2% to about 8% or more, from about 3% to about 7% or more, and from 4% to about 6% or more, and about 5%.

In further embodiments, the drug delivery systems and compositions of the present invention further comprise one or more excipients, for example, pharmaceutically, or physiologically, acceptable organic, or inorganic carrier substances suitable for enteral or parenteral application which do not deleteriously react with the composition. Suitable pharmaceutically acceptable carriers include water, salt solutions (such as Ringer's solution), alcohols, oils, gelatins and carbohydrates such as lactose, amylose or starch, fatty acid esters, hydroxymethylcellulose, and polyvinyl pyrolidine. Such preparations can be sterilized and, if desired, mixed with auxiliary agents such as lubricants, preservatives, stabilizers, wetting agents, emulsifiers, salts for influencing osmotic pressure, buffers, coloring and/or aromatic substances and the like which do not deleteriously react with the compositions administered to the human. Certain methods of the present invention provide readily scalable production schemes for producing drug carrier compositions and drug delivery platforms with enhanced efficiency.

Still other embodiment of the present invention provide production schemes for producing polymeric drug delivery platforms at scale while maintaining current Good Laboratory Practice ("cGLP"), and/or current Good Manufacturing Practice ("cGMP") standards, related to experimental and non-clinical trial materials, compared to clinical trial materials, respectively.

Preferred embodiments of the instant compositions provide drug carrier compositions (e.g., nanospheres) ranging in size from about 5 nm to about 500 nm, and more preferably about 50 nm or less. Standard techniques can be used to concentration and/or filter nanospheres.

DESCRIPTION OF THE INVENTION

The present invention relates generally to hybrid polymer (e.g., polyphosphazene) based drug delivery platforms and to methods of producing, evaluating, administering, and treating subjects with the same. More particularly, the present invention provides polyphosphazene based drug delivery platforms comprising one or more polyphosphazenes with controlled molecular weights and/or polydispersities as well as selective methods for associating one or more therapeutic drug (or prodrug) substances to the polyphosphazenes.

Further provided are processes for preparing polyphosphazenes that include a cationic solution polymerization reaction of a phosphoranimine, using a main group or transition metal halide, or other appropriate halide salt, including a linear phosphazene salt of any chain length, or a preformed non-phosphazene polymer containing a main or transition metal chloride, as an initiator. In certain preferred embodiments, triarmed-star polyphosphazenes having the formula $N\{RN(H)R'_2P\text{---}(N\!=\!PR'_2)_n\}_3$ are prepared via this method. Also, provided are methods for synthesis of the monomer $Cl_3P\!=\!NSiMe_3$ and cyclic trimer $N_3P_3X_6$ from the reactants $N(SiR_3)_3$ and $PX_5$.

A process for the preparation of polyphosphazenes is provided that includes the cationic solution polymerization reaction of a phosphoranimine, using a main group or transition metal halide, or other appropriate halide salt, including a linear phosphazene salt of any chain length as an initiator.

This process represents a significant advance in the art of synthesis of polyphosphazenes, in that it provides a new degree of control over the molecular weight of the product, and provides a product with narrow polydispersity. Poly(dichlorophosphazene) with a polydispersity of 1.6 or less (for example, 1.4, 1.2, 1.1, or 1.05 or less), and corresponding poly(organophosphazenes) with a polydispersity of 1.2 (for example, 1.1 or 1.05) or less can be prepared using this method.

This invention is disclosed in the following description, and is illustrated in the working examples. The working examples are merely illustrative of selected specific embodiments of the invention, and are not intended to be construed to limit its scope. Given the disclosure, one of ordinary skill in the art can routinely modify the process as necessary or desired.

I. Definitions

The terms "drug," "drug substance," "active drug substance," or "biological agent," as used herein, refer to organic and/or inorganic molecules including, but not limited to, small molecule drugs, proteins, polysaccharides, nucleoproteins, lipoproteins, synthetic polypeptides, small molecules linked to a protein(s), saccharides, oligosaccharides, carbohydrates, glycoploymers, glycoproteins, steroids, nucleic acids, nucleotides, nucleosides, oligonucleotides (including antisense oligonucleotides), cDNA, nucleic acids, vitamins, including, but not limited to, vitamin C and vitamin E, lipids, or combination and portions thereof, that causes a biological effect when administered in vivo to an animal such as mammal and in particular, a human. As used herein, these terms more particularly in certain embodiments, further refer to any substance used internally or externally in an animal (e.g., a human) as medicaments, medicines, or prophylactics (i.e., vaccines and immunological active compositions) for the treatment, cure, or prevention of a disease, disorder, or medical condition, including, but not limited to, antifungal, agents (e.g., Fluconazole and Voriconazole), antiepileptic drugs (e.g., Rufinamide and Topiramate), immunosuppressants, antioxidants, anesthetics, chemotherapeutic agents, steroids (e.g., retinoids, hormones and the like), antibiotics, antivirals, antiproliferatives, antihistamines and allergy treatments (e.g., Triamcinolone acetonide), anticoagulants, antiphotoaging agents, biological agents (e.g., nucleotides, oliogonucleotides, polynucleotides, and nucleic acid sequences (e.g., DNAs and/or RNAs, and derivatives thereof), amino acids, oligopeptides, polypeptides, and proteins (e.g., therapeutic peptides and proteins, and antibodies and fragments and derivatives thereof, and the like), bisphosphonates, melanotropic peptides, nonsteroidal and steroidal anti-inflammatory compounds, and targeted cancer drugs. In other embodiments, suitable chemotherapeutic agents include, but are not limited to, small molecule chemotherapeutic drugs and anticancer and/or anti-tumorigenic agents, antiproliferative agents, antiangiogenic agents, anti-metastatic agents, neoadjuvant therapies and agents, immunological therapies (e.g., "checkpoint inhibitor" agents)).

The term "aliphatic," as used herein, refers to a hydrocarbon, typically of $C_1$ to $C_{20}$, that can contain one or a combination of alkyl, alkenyl, or alkynyl moieties, and which can be straight, branched, or cyclic, or a combination thereof. A lower aliphatic group is typically from $C_1$ to $C_5$.

The term "alkyl," as used herein, unless otherwise specified, refers to a saturated straight, branched, or cyclic, primary, secondary, or tertiary hydrocarbon, preferably of $C_1$ to $C_{20}$, and specifically includes methyl, ethyl, propyl, isopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The alkyl group can be optionally substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al. ("Protective Groups in Organic Synthesis," John Wiley and Sons, Second Edition, 1991). The term "lower alkyl," as used herein, refers to an alkyl group of $C_1$ to $C_5$.

The term "alkylamino" or "arylamino" refers to an amino group that has one or two alkyl or aryl substituents, respectively.

The term "protected," as used herein, and unless otherwise defined, refers to a group that is added to an oxygen or nitrogen atom to prevent its further reaction during the course of derivatization of other moieties in the molecule in which the oxygen or nitrogen is located. A wide variety of oxygen and nitrogen protecting groups are known to those skilled in the art of organic synthesis.

The term "amino acid," as used herein, refers to a natural or synthetic amino acid, and includes, but is not limited to alanyl, valinyl, leucinyl, isoleucinyl prolinyl, phenylalaninyl, tryptophanyl, methioninyl, glycinyl, serinyl, threoninyl, cysteinyl tyrosinyl, asparaginyl, glutaminyl, aspartoyl, glutaoyl, lysinyl, argininyl, and histidinyl. The term "amino acid ester" refers to the aliphatic, aryl or heteroaromatic carboxylic acid ester of a natural or synthetic amino acid.

The term "aryl," as used herein, and unless otherwise specified, refers to phenyl, biphenyl, or naphthyl, and preferably phenyl. The aryl group can be optionally substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis," John Wiley and Sons, Second Edition, 1991.

As used herein, the term "halo" includes chloro, bromo, iodo, and fluoro.

The terms "heteroaryl" or "heteroaromatic," as used herein, refer to an aromatic moiety that includes at least one sulfur, oxygen, or nitrogen in the aromatic ring. Non-limiting examples are furyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbozolyl, oxazolyl, thiazolyl, isothiazolyl, 1,2,4-thiadiazolyl, isooxazolyl, pyrrolyl, quinazolinyl, pyridazinyl, pyrazinyl, cinnolinyl, phthalazinyl, quinoxalinyl, xanthinyl, hypoxanthinyl, pteridinyl, 5-azacytidinyl, 5-azauracilyl, triazolopyridinyl, imidazolopyridinyl, pyrrolopyrimidinyl, pyrazolopyrimidinyl, adenine, $N^6$-alkylpurines, $N^6$-acylpurines (wherein acyl is C(O) (alkyl, aryl, alkaryl, or aralkyl)), $N^6$-benzylpurine, $N^6$-halopurine, $N^6$-vinylpurine, $N^6$-acetylenic purine, $N^6$-acyl purine, $N^6$-hydroxyalkyl purine, $N^6$-thioalkyl purine, thymine, cytosine, 6-azapyrimidine, 2-mercaptopyrimidine, uracil, $N^5$-alkylpyrimidines, $N^5$-benzylpyrimidines, $N^5$-halopyrimidines, $N^5$-vinylpyrimidine, $N^5$-acetylenic pyrimidine, $N^5$-acyl pyrimidine, $N^5$-hydroxyalkyl purine, and $N^5$-thioalkyl purine, and isoxazolyl. Functional oxygen and nitrogen groups on the heterocyclic base can be protected as necessary or desired during the reaction sequence. Suitable protecting groups are well known to those skilled in the art, and include trimethylsilyl, dimethylhexylsilyl, t-butyldimethylsilyl, and t-butyldiphenylsilyl, trityl, alkyl groups, acyl groups such as acetyl and propionyl, methylsulfonyl, and p-toluylsulfonyl.

The terms "alkylheterocyclic" or "alkylheteroaromatic" refer to a moiety in which the alkyl group is covalently attached to the heteroaromatic, is preferably $C_1$ to $C_4$ alkylheteroaromatic, and more preferably $CH_2$-heteroaromatic.

The term "aralkyl," as used herein, refers to an aryl group with an alkyl substituent.

The term "alkoxy," as used herein, and unless otherwise specified, refers to a moiety of the structure —O-alkyl.

The term "alkynyl," as referred to herein, refers to a $C_2$ to $C_{10}$ straight or branched hydrocarbon with at least one triple bond.

The term "protected-oxy" refers to an oxygen atom that has been protected from undesired reactions with any of the oxygen protecting group known to those skilled in the art, including but not limited to, for example, a trisubstituted silyl group such as trimethylsilyl, dimethylhexylsilyl, t-butyldimethylsilyl, t-butyldiphenylsilyl, trityl, alkyl group, acyl groups such as acetyl, propionyl, benzoyl, p-NO$_2$ benzoyl, toluyl, methylsulfonyl, or p-toluylsulfonyl.

As used herein, the term "heteroalkyl" refers to an alkyl group that includes a heteroatom such as oxygen, sulfur, or nitrogen (with valence completed by hydrogen or oxygen) in the carbon chain or terminating the carbon chain. Examples of these compounds include a series of lower alkyls interrupted by a heteroatom such as oxygen, sulfur or nitrogen, including —O—[(alkyl)O]$_x$—CH$_2$)NH$_2$, wherein the alkyl group can vary within the moiety, including —O—[(CH$_2$)$_x$O]$_y$—CH$_2$)$_x$NH$_2$; —O—[(CH$_2$)$_x$O]$_y$CH$_2$)$_x$NH(CH$_2$)$_x$SO$_3$H, and —O—[(alkyl)-O]$_y$-(alkyl), wherein the alkyl group can vary within the moiety, including —O—[(CH$_2$)$_x$O]$_y$-(alkyl), wherein x is 1-8 (which can vary within the moiety) and y is an integer of 1 to 40. Specific examples of these compounds include (methoxyethoxy)ethoxy, ethoxyethoxy and methoxyethoxy. The heteroalkyl groups can also be halogenated such as —OCH$_2$CF$_3$ and the like.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended; that is, a composition, article, or process that includes elements in addition to those listed after such a term in a claim are still deemed to fall within the scope of that claim. Moreover, in the following claims, the terms "first," "second," and "third," and so forth are used merely as labels, and are not intended to impose numerical requirements on their objects.

Recitation of ranges of values herein are merely intended to serve as a shorthand method of referring individually to each separate value falling within the range, unless otherwise indicated herein, and each separate value within the range is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Unless otherwise defined herein, technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. In this application, the use of "or" means "and/or" unless stated otherwise.

Although the embodiments of the present invention have been described with reference to specific example embodiments, it will be evident that various modifications and changes may be made to these embodiments without departing from the broader scope of the inventive subject matter. Accordingly, the specification and Figures are to be regarded in an illustrative rather than a restrictive sense. The accompanying Figures that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be used and derived therefrom, such that structural and logical substitutions and changes may be made without departing from the scope of this disclosure. The Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

That the present invention may be more readily understood, select terms are defined below.

II. Selection of Phosphoranimine

A phosphoranimine is used as the monomer in the preparation of the polyphosphazene. In a preferred embodiment, the phosphoranimine is of the structure: $R_3P=NSi(R')_3$ wherein at least one R substituent is chloro, fluoro, bromo, or iodo, and preferably chloro, and the remaining R and R' substituents are any groups that do not contain functional moieties that would adversely affect the polymerization process.

In a preferred embodiment, at least two R substituents are halo, and preferably chloro. A preferred phosphoranimine is trichloro(trimethylsilyl)phosphoranimine, $Cl_3P=NSiMe_3$. Examples of moieties that do adversely affect the polymerization process include —NH, —OH, acidic groups, bases, labile fluorine atoms, organolithium reagents and Grignard reagents. At least some of these moieties can be converted into noninterfering groups by conventional protection, followed by deprotection at an appropriate time. The interfering groups are typically those that react with the propagating end group, presumably the $PCl_3^+ \cdot PCl_6^-$ unit.

In one embodiment, R is independently (and protected as necessary) chloro, bromo, iodo, aliphatic, including alkyl, alkenyl, or alkynyl; aralkyl, alkaryl, aryl, heteroalkyl, heteroaryl, cyano, amino acid ester, carboxylic acid ester, -oxyaryl including but not limited to -oxyphenyl-p-methyl, protected -oxyphenyl$CO_2H$, protected -oxyphenyl$SO_3H$, -oxyphenylhydroxyl and -oxyphenyl$PO_3H$; oxyaliphatic, including -oxyalkyl, -oxy(aliphatic)$CO_2H$, -oxy(aliphatic)$SO_2H$, -oxy(aliphatic)$PO_3H$, and -oxy(aliphatic)hydroxyl, including -oxy(alkyl)hydroxyl; -oxyalkaryl, -oxyaralkyl, -thioaryl, -thioaliphatic including -thioalkyl, -thioalkaryl, aliphatic and aryl ketone, phosphine oxide or phosphoryl compound (P=O), ether, sulfone and sulfoxide.

If the R group attached to the phosphorus atom is bulky, it may affect the tacticity of the polymer. For example, one may obtain a syndiotactic or isotactic polyphosphazene by appropriate selection of the R group. Bulky groups such as aryl or napthyl groups may polymerize in a syndiotactic arrangement. The large groups may preferentially alternate the side of the phosphorus they are on to minimize steric interactions.

R' is preferably independently aliphatic, preferably lower alkyl, aryl, aralkyl, or alkaryl. In a preferred embodiment, R' is lower alkyl. Non-limiting examples of the —$Si(R')_3$ moiety include trimethylsilyl, triphenylsilyl, aryldialkylsilyl, and t-butyldimethylsilyl.

During the reaction, one of the R groups on the phosphorus of the phosphoranimine, typically a halogen such as chlorine, will be removed and the remaining two R groups on the phosphorus atom will become the substituents on the resulting polyphosphazene. For example, if a —$PCl_3$ moiety is present in the phosphoranimine, a poly(dichlorophosphazene) will be produced. If, for example, a —$PCl_2$ alkyl or —$PC_2$ aryl group is present, a —$[N=P(Cl(alkyl)]_n$— or —$[N=P(Cl(aryl)]_n$—, respectively, will be produced.

A phosphoranimine should be selected that is stable to trimerization. If the substituent groups are collectively too large, a trimer is favored over a polymer. However, if the initiator is a linear phosphazene longer than three repeat units, the molecule cannot trimerize. However, under certain circumstances, it is possible that initiators of this size can inhibit polymerization.

In one embodiment, at least one R' group is selected that is chiral, to promote chiral polymerization. If the anion is chiral and maintains a close association with the chain end, the anion may affect the tacticity of the polymer chain. An example is $PCl_4R'$ where R is chiral. The phosphoranimine is $Cl(R)(R')P=NTMS$, where R does not equal R'. Phosphoranimines can be prepared according to known methods.

III. Selection of Initiator

The polymerization initiator is a cationic species that contains a halide counterion, preferably chloride, that will facilitate the removal of —$Si(R')_3$ from the phosphoranimine. In one embodiment, the reaction initiator is a main group or transition metal halide, or other appropriate halide salt. For example, the initiator can be $MX_nY_m$ or $EX_nY_m$, wherein M is a transition metal element (including, but not limited to: V, Cr, Zr, Nb, Hf, Ta, W, Mo, Mn, Fe, Ru, Os, Co, Rh, Ir, Ni, D Pd, Pt, Cu, Zn, Cd and Hg), E is a main group element (including, but not limited to P, Si, As, Sb and Ge), X is a halide, Y is any inorganic or organic substituent that does not adversely affect the initiation or polymerization reaction (including but not limited to aliphatic such as alkyl, and aryl), n is 1 to the valence state of M or E, and m is the valence state minus n. For example, in phosphorous pentachloride ($PCl_5$), the valence state of phosphorous is 5, and in $WX_6$, the valence state of W is 6. Examples are $PCl_5$, $TiCl_4$ (which may lead to branched polymers), $TaCl_5$ (slower than $PCl_5$), $SO_2Cl_2$, $AlCl_3$, $VCl_4$, $BF_3$, $SnCl_4$, $SbCl_5$, $ZnCl_4$, $(Ph)_3CPF_6$, $(Ph)_3CSbF_6$, $(Ph)_3CPCl_6$, $(Ph)_3CSbCl_6$, oxyhalides such as $POCl_3$, $CrO_2Cl$, $SOCl_2$, and $VOCl_3$. Non-limiting examples of linear phosphazene salts that can be used as initiators are $Cl_3P=N—PCl_3+A^-$, wherein A is any counteranion that does not adversely affect the reaction (including but not limited to halo, $PX_6$), and preferably chloride or $PCl_6$; and $(R)Cl_2P=N—(PCl_3)^+A^-$, for example, $RCl_2P=N—PCl_3PCl_6^{31}$.

In an alternative embodiment, a linear phosphazene salt is used as an initiator that is in itself an oligomer. For example, the salt $[Cl_3P=N—PCl_3]^+[PCl_6]^-$ can be reacted with a selected ratio of equivalents of $Cl_3P=NSiMe_3$ to produce longer cationic P—N chains. Linear phosphazene salts of seven monomeric units are typically the highest in the oligomer series that can be obtained as single products. Above this, mixtures of 9 and 11, or 11 and 13, or 11, 13 and 15 member chains are typically obtained. The series of addition reactions leads to a clean stepwise synthesis of various P—N salts by the elimination of $ClSiMe_3$. To obtain the 3, 5 and 7 member chains, one equivalent at a time is added. However, to obtain larger chains, all of the equivalents can be added at once. Other oligomeric phosphazene salts, such as $[RCl_2P=N—PCl_3^+]A^+$ and $R_3P—[N=P(R')_2]_z$ $N=PR'_2Cl^+$ $A^-$ where z is 1-7 can be prepared analogously. The use of a linear oligomeric phosphazene salt as an initiator represents one method for the preparation of a polyphosphazene block copolymer.

Among the advantages of the use of a linear phosphazene salt is that it is easier to purify and easier to functionalize than metal salts. Further, the solubility of the phosphazene salt can be increased by increasing the chain length as desired.

Example 1

Preparation of Trichloro(trimethylsilyl)phosphoranimine

The synthesis of trichloro(trimethylsilyl) phosphoranimine $Cl_3P=N-SiMe_3$ is reported in Honeyman, C Route to New Inorganic Rings and Polymers; The Reactions of $Cl_2RP=NSiMe_3$, (R=Cl or Ph) with Main Group and Transition Metal Chlorides MS Thesis, Department Of Chemistry, University of Toronto, 1992. The synthesis involves the dropwise addition of a single equivalent of $LiN(SiMe_3)_2$ in hexanes to a vigorously stirred cold (−78° C.) slurry of $PCl_5$ in hexane. A major challenge was the need to obtain $Cl_3P=N-SiMe_3$ in high purity. The monomer formed by this route did not polymerize in a reproducible manner when treated with trace amounts of $PCl_5$ in $CH_2Cl_2$ $^1H$ NMR spectra and mass spectrometry (Cl-MS revealed the presence of $(Me_3Si)_2NCl$ as a side product. This species appears to inhibit polymerization. Multiple distillations did not remove $(Me_3Si)_2NCl$ because this compound distills at a similar temperature and pressure to $Cl_3P=N-SiMe_3$. Pure $Cl_3P=N-SiMe_3$ was obtained by treatment of the mixture with $PPh_3$ (in an excess or stoichiometric amount relative to $(Me_3Si)_2NCl$ in $CH_2Cl_2$ to form $Ph_3P=NSiMe_3$ and $Me_3SiCl$. The resultant mixture was then distilled at reduced pressure to yield pure $Cl_3P=N-SiMe_3$. Purification of the reaction products by distillation gives the product as a clear, colorless, moisture sensitive liquid distillate.

Alternatively, to avoid the additional purification step, $Cl_3P=N-SiMe_3$ has also been obtained from the reaction of $PCl_5$ with $N(SiMe_3)_3$ in hexane at −78° C. Although this synthesis generated no $(Me_3Si)_2NCl$ impurity, the yields of $Cl_3P=N-SiMe_3$ produced via this route have not been optimized.

Example 2

Reaction of $N(SiMe_3)_3$ with $PCl_5$ to form $Cl_3P=NSiMe_3$

Tris(trimethylsilyl)amine was synthesized as previously reported in the literature. Chlorotrimethylsilane was added slowly to lithium bis(trimethylsilyl amide) in tetrahydrofuran stirred with a magnetic stirrer and cooled with an ice bath. After all of the chlorotrimethylsilane was added, the reaction was heated to reflux for 48 hours. After the reaction cooled to room temperature, the LiCl formed was filtered using an airless fritted funnel. The solvent was evaporated under reduced pressure using a dry ice/acetone trap. The remaining solid was then sublimed to give a clear colorless product.

Phosphorus pentachloride (22.29 g) was stirred in hexane (300 mL) at 0° C. Tris(trimethylsilyl) amine (25.00 g) dissolved in hexane (200 mL) was added to the solution dropwise. The reaction was allowed to slowly warm to room temperature, stirred for 24 h, and filtered. Fractional distillation of the filtrate at room temperature and reduced pressure provided $Cl_3P=NSiMe_3$ in a 30% yield.

Example 3

Reaction of $N(SiMe_3)_3$ with $PCl_5$ to form $N_3P_3Cl_6$

Tris(trimethylsilyl) amine (34.00 g) was dissolved in dichloromethane (300 mL), stirred with a magnetic stirrer, and heated to reflux. Phosphorus pentachloride (30.31 g) dissolved in dichloromethane (300 mL) was added to the solution dropwise. After all of the solution had been added, the solvent was removed under vacuum to provide a solid material that was 76% trimer, 4% tetramer, 3% pentamer, and 13% higher cyclics and oligomers.

In order to promote the formation of trimer $N_3P_3Cl_6$, the key is to add $PCl_5$ to $N(SiMe_3)_3$ very slowly at reflux in a polar solvent, such as methylene chloride, to allow the linear $Cl_3PNP(Cl)_2NPCl_3{}^+PCl_6{}^-$ salt to react with $N(SiMe_3)_3$ to form the cyclic trimer. If $PCl_5$ is added too quickly, the thermodynamically favorable tetramer becomes the primary product.

Example 4

Preparation of Dichloro(phenyl)(trimethylsilyl)phosphoranimine $Cl_2PhP=N-SiMe_3$ The procedure used to prepare this compound was analogous to that described in Example 1 for $Cl_3P=N-SiMe_3$ except as follows. To tetrachlorophenylphosphorane (80 g, 0.32 mol) in hexanes (1000 ml) at −78° C. was added dropwise a solution of lithium bistrimethylsilyl)amide, LiN(SiMe_3)_2(53 g, 0.32 mol) in hexanes (500 ml) with mechanical stirring. The clear, colorless product was distilled (bp 53° C., 0.02 mm Hg) and was identified as $Cl_3PhP=N-SiMe_3$. Yield 47.0 g (55%). $^{31}P$ NMR ($CH_2Cl_2$) Δ-11.8 ppm; $^{13}C$ NMR ($CDCl_3$) Δ133.2 ppm (Δ, $4J_{CP}=4$ Hz, p-Ph), Δ130.7 ppm (Δ, $3J_{CP}$-13 Hz, m-Ph), Δ128.7 ppm ($A^2J_{CP}=19$ Hz, o-Ph), Δ1.9 PPM (Δ, $^4J_{CP}=7$ Hz, $CH_3$), ipso-Ph not observed; $^1H$ NMR ($CDCl_3$)d 8.0 ppm (Δ, of Δ, $^3J_{HP}=19$ Hz, $^2J_{HH}$ (om)=Hz, 2H, o-Ph), A, 7.5 ppm (br., 3H, p- and m-Ph), Δ 0.2 ppm (Δ, $^4J_{HP}=3$ Hz, 9H, $CH_3$).

Example 5

Preparation of $[Cl_3P=N-PCl_3][PCl_6]$ By Reaction of 2 Equivalents of $PCl_5$ with 1 Equivalent of $Cl_3=N-SiMe_3$ Two equivalents of phosphorus pentachloride (3.6 g, 17 mmol) were dissolved in dichloromethane (50 ml) and the resulting stirred solution was cooled to −78° C. A single equivalent of $Cl_3P=N-SiMe_3$ (2.0 g, 9 mmol) was added quickly to the syringe and the reaction mixture was immediately allowed to warm to room temperature. The solvent was removed in vacuo resulting in a fine white powder which was identified as $[Cl_3P=N-PCl_3][PCl_6]$. Yield 4.3 g (90%). $^{31}P$ NMR ($CH_2Cl_2$) Δ22.4 ppm (=$PCl_3$), A-293.6 ($[PCl_6]^-$).

Example 6

Preparation of $[Cl_3P=N-PCl_2-N=PCl_3]^{+-}[PCl_6]^-$ By Reaction of 1 Equivalent of $[Cl_3P=N-PCl_3]^+[PCl_6]^-$ with 1 Equivalent of $Cl_3P=N-SiMe_3$ The salt $[Cl_3P=N-PCl_3]+[PCl_6]1$ (1.5 g, 3 mmol) was dissolved in dichloromethane (50 ml) and the resulting stirred solution was cooled to −78° C. $Cl_3P$=N—$SiMe_3$ (2.0 g, 9 mmol, 1eq.) was added quickly by syringe and the reaction mixture was immediately allowed to warm to room temperature. The solvent was removed in vacuo resulting in a fine white powder which was identified as [$Cl_3P$=N—$PCl_2$—N=$PCl_3$]$^+$[$PCl_6$]$^-$. Yield 1.8 g (92%). $^{31}$P NMR ($CH_2Cl_2$) Δ14.6 ppm (d, $^2J_{PP}$ 45 Hz)=$PCl_3$, Δ-10.5 ppm (t, $^2J_{PP}$ 45 Hz)-$PCl_2$,—, Δ-293.6 ppm [$PCl_6$]$^-$.

IV. Conditions of Polymerization

The disclosed route for the preparation of polyphosphazenes provides an opportunity for control over polymer molecular weight and structure, and allows access to polyphosphazenes with narrow polydispersities. The synthetic route described herein can produce products ranging from oligomers to high molecular weight polymers. A typical molecular weight range of the polymers is between approximately $10^3$ and $10^6$, but others outside this range can also be prepared. Importantly, the process can be carried out at or near ambient temperatures.

The route described herein for the preparation of polyphosphazenes is considerably less complicated and less expensive in terms of the chemicals required and the temperatures needed than any of the alternatives currently available. Moreover, the relative ease of preparation and the access to new polyphosphazenes are of fundamental importance in the field of polyphosphazene chemistry both academically and industrially.

This method allows for the recycling of $ClSiMe_3$, which is important economically and environmentally. This, together with the large scale availability of the starting materials $ClSiMe_3$ and $PCl_5$ or $RPCl_4$ offers favorable prospects for the large scale synthesis of polyphosphazenes and for a marked expansion in the availability and utility of poly(phosphazenes).

The procedure for carrying out the solution reaction is quite simple and easy to accomplish on a manufacturing scale. The selected phosphoranimine is mixed with solvent, and then a small amount of initiator is added, and the solution is stirred.

It is important that the reaction mixture be a homogeneous solution in order to obtain a narrow PDI. The initiator, and phosphoranimine, initial oligomers formed and polymer product should be soluble to maintain molecular weight control and a narrow PDI. Therefore, solubility limits the choice of monomer and initiator. It is preferable to pretreat glass or glass-lined reaction vessels with a silating reagent such as $ClSiMe_3$ prior to running the reaction.

The reaction is carried out in any organic solvent that does not adversely affect the polymerization reaction, i.e., it must be inert under the conditions of reaction. It should also be dry. Dichloromethane and other halogenated inert solvents are preferred solvents for the solution synthesis of poly (dichlorophosphazene). Other suitable solvents include, but are not limited to, glyme, diglyme, toluene, acetonitrile, dioxane, and cyclohexane.

The choice of solvent will affect the molecular weight distribution of the product. If dioxane is used, multimodal GPC traces can be obtained. If too little solvent is used (for example, not enough to bring all of the reactants into solution) the polymerization can resemble that occurring under neat (i.e., bulk) conditions with resulting multimodal GPC traces.

The reaction can be carried out at any desired temperature that does not unduly affect the reactants or product. Importantly, most of the polymerization reactions do not require heat at all. The reaction is typically carried out at a temperature ranging between 2° and 23° C.

The molecular weight of the product can be controlled, for example, by the choice of initiator, the monomer/initiator ratio, by the addition of monomer to preformed active or living chains, or by the control of the time of the reaction.

Any ratio of phosphoranimine to initiator can be used that provides the desired product. In one embodiment, between 100 and 5 moles of monomer to 1 mole of initiator are used, and preferably, between 20 and 5 moles of monomer. As the ratio of initiator to phosphoranimine increases, the molecular weight of the product decreases. $PCl_5$ and $Cl_3PNPCl_3^+A^-$ are preferred initiators.

The reaction is carried out for any amount of time that provides the desired product. In general, reaction times of between approximately 6 and 24 hours are typical, however, the polymerization reaction may be complete in under two hours.

The reaction can be carried out at ambient pressure or reduced pressure, in air or in an inert atmosphere such as $N_2$, as appropriate for the starting material and product.

The control over molecular weight and the very narrow polydispersity that can be obtained using this method distinguishes it from the corresponding bulk (i.e., without solvent) method, as described in more detail in Example 7.

Example 7

Comparison of Bulk and Solution Polymerization of Phosphoranimine

It was postulated that the treatment of $Cl_3P$=$NSiMe_3$ with trace quantities of $PCl_5$ might afford high molecular weight poly(dichlorophosphazene), and that control over the ratio of the phosphoranimine to $PCl_5$ might allow for the control of the molecular weight of the polymer produced. The addition of trace $PCl_5$ (ca 10 mg) to pure $Cl_3P$=$NSiMe_3$ (1.0 g) at room temperature led after 5 days to the formation of a two-phase mixture. Both phases were clear and colorless but the upper more fluid layer, was found, by $^1$H NMR spectroscopy to consist mainly of $Me_3SiCl$. A $^{31}$P NMR spectrum of the entire tube contents showed predominantly a sharp singlet characteristic of poly(dichlorophosphazene). Thus, the conversion of $Cl_3P$=$NSiMe_3$ to linear polymer was essentially quantitative. The poly(dichlorophosphazene) product was treated with an excess of $NaOCH_2CF_3$, and the resultant polymer gave a $^{31}$P NMR signal characteristic of a well known polymer, [N=$P(OCH_2CF_3)_2]_n$. Analysis of this polymer by gel permeation chromatography (GPC) indicated that it possessed only a high molecular weight fraction having $M_w$=2.1×$10^5$ and a polydispersity index (PDI=$M_w/M_n$)=1.8 versus polystyrene standards. However, in subsequent attempts to obtain lower molecular weight poly(dichlorophosphazene) by increasing the ratio of $PCl_5$ to monomer with the same solvent-free conditions, the initiator and initial cationic products remained primarily insoluble. The molecular weight values of the polymers produced were lower than in the above experiment, but the GPC trace of this polymer was multimodal. The results suggested a lack of molecular weight control in the solvent-free system due to the heterogeneous nature of the process.

In contrast, the reaction of $Cl_3P$=$NSiMe_3$ with traces of $PCl_5$ in a methylene chloride solution resulted in a quantitative conversion to poly(dichlorophosphazene) (as estimated by $^{31}$P NMR spectroscopy and GPC analysis of the trifluoroethoxy derivatives [N=$P(OCH_2CF_3)_2]_n$) with a very narrow polydispersity. An increase in the ratio of phosphoranimine to $PCl_5$ in solution resulted in an increase in the molecular weight while still retaining narrow PDI values, as indicated in Table 1 below.

TABLE 1

| Sample | $PCl_3$ | $Cl_3$=$NSiMe_3$ | Mon/Init | $N_w$ | PDI |
|---|---|---|---|---|---|
| Bulk 1 | ~10 mg | 1.0 g | 100 | 21000 | 1.8 |
| Bulk 2 | 110 mg | 1.6 g | 14.5 | 41000 | 2.3* |
| Solution 3 | 200 mg | 1.0 g | 5 | 7000 | 1.20 |
| Solution 4 | 100 mg | 1.0 g | 10 | 11000 | 1.04 |
| Solution 5 | 29 mg | 0.6 g | 21 | 14000 | 1.04 |

*multimodal GPC trace

The analogous reaction between a trace of $PCl_5$ and $PhCl_2P$=$NSiMe_3$ in the bulk state at room temperature also yielded a polymeric product. In this case the polymerization resulted in the formation of poly[aryl(chloro)phosphazene], [N=P(Ph)Cl]n which was converted to the known macromolecule $[N=P(Ph)(OCH_2CF_3)]_n$ with $M_n=8.0\times10^4$ and polydispersity of 1.4. An investigation into the effect of monomer to initiator ration of the molecular weight polymerization of $Cl_3P$=$N$—$SiMe_3$ was conducted. The results (see Table 2 below) show an increase in the ratio of phosphoranimine to $PCl_5$ in solution brought about an increase in the molecular weight, while still retaining narrow PDI values.

TABLE 2

| M:I | $M_n \times 10^{-3}$ Found[a] | Mn $\times 10^{-3}$ Calculated[b] | PDI |
|---|---|---|---|
| 4.6:1 | 5.8 | 2.5 | 1.20 |
| 9.3:1 | 10.6 | 5.0 | 1.04 |
| 23:1 | 20.2 | 12 | 1.09 |
| 46:1 | 53.0 | 24 | 1.32 |
| 70:1 | 66.4 | 36 | 1.25 |

[a]Obtained by GPC vs polystyrene
[b]Calculated from the initial ratio of monomer to $PCl_5$ initiator Example 8

Preparation of Poly(dichlorophosphazene) from Trichloro(trimethylsilyl)phosphoranimine The solution polymerization of trichloro(trimethylsilyl) phosphoranimine was carried out according to the following general procedure. All glassware was pretreated with 5% $ClSiMe_3$ in hexanes and dried under vacuum. The $Cl_3P$=$NSiMe_3$ was sublimed prior to use and stored under nitrogen. A solution of $PCl_5$ (100 mg) in $CH_2Cl_2$ (10 mL) was added to a stirred solution of $Cl_3P$=$NSiMe_3$ (1.0 g, 4.4 mol) in $CH_2Cl_2$ (35 mL) under nitrogen. The solution was stirred for 24 hours. The products were analyzed by $^{31}P$ NMR.

The analyses were performed using the techniques and instruments set forth below. $^1H$ NMR (360.0 MHz), $^{13}C$ NMR (90.0 20 MHz), and $^{31}P$ NMR (145.8 MHz) spectra were obtained using a Bruker WM-360 MHz spectrometer. Chemical shifts are relative to tetramethylsilane at δ=0 for proton and carbon. The phosphorus chemical shifts are relative to 85% $H_3PO_4$ at δ=0, with positive shift values downfield from the reference. All heteronuclear NMR spectra were proton decoupled.

Molecular weights were determined using a Hewlett Packard HP 1090 gel permeation chromatograph equipped with an HP1037A refractive index detector and Polymer Laboratories PL gel 10 μm columns. The samples were eluted with a 0.1% by weight solution of tetra-n-butylammonium bromide in THF. The GPC column was calibrated with polystyrene standards (Waters) the results are provided in Table 1.

Example 9

Preparation of Polychloro(phenyl)phosphazene from Dichloro(phenyl)(trimethylsilyl) phosphoranimine Polychloro(phenyl)phosphazene was prepared according to the bulk polymerization method described in Example 7, using $Cl_2PhP$=$NSiMe_3$ instead of $Cl_3P$=$NSiMe_3$. Treatment of this polymer with sodium trifluoroethoxide resulted in a polymer identical with literature reports. The weight average molecular weight was $3.0\times10^4$ and the polydispersity ($M_w/M_n$) was 1.4.

Example 10

Evidence for Macrocondensation

Samples of poly(dicholorophosphazene) that were not subjected to halogen replacement immediately following complete conversion of monomer, but instead were maintained for several days at 25° C. before being substituted, showed a change in molecular weight distribution. GPC chromatograms consisted not of a single sharp peak as expected, but a peak with a higher molecular weight shoulder. The shoulder corresponded to approximately twice the molecular weight of the original peak. This occurred for several monomer to initiator ratios, and suggested a macrocondensation reaction in which two polymer chains join together to form a single polymer of twice the molecular weight. In order to study this phenomenon, a polymerization experiment was conducted with a 23:1 1:$PCl_5$ ratio sample. The polymerization solution was divided into two equal parts. The first sample was treated with $NaOCH_2CF_3$ in dioxane immediately after conversion of the monomer to polymer. The GPC chromatogram of this substituted polymer 2 contained one sharp peak that corresponded to values of $M_n=2.0\times10^4$ and PDI=1.09. The second sample was not substituted, but was stirred at 25° C. for 20 days in the $[N=PCl_2]_n$ form. It was then treated with $NaOCH_2CF_3$ in dioxane to produce polymer with $M_n=2.2\times10^4$ and PDI=1.17. However, the GPC chromatogram of this polymer had an additional high molecular weight shoulder at approximately twice the molecular weight of the first polymer. This suggests that $[N=PCl_2]_n$ macrocondensation can occur over time. A possible mechanism for this process is hydrolytic coupling of two polymer chains to give a macromolecule with a molecular weight twice that of the original. Another possibility is the coupling of two neutral chain ends ($Cl_3P$=$N$—) to form a dimeric species. Thus, in order to obtain controlled molecular weight polymers, it is essential to substitute the polymer immediately after complete conversion of monomer or to store the material at temperatures below 0° C.

V. Endcaps

The chain ends of the growing polymer in this process are active throughout the duration of the polymerization as well as active after the total consumption of the monomer. By "active" it is meant that the ends are in a reactive state, and specifically, in a cationic state. They are thus available as additional reaction sites for polymerization or derivatization.

In one embodiment, a desired moiety is reacted with the cation polymer end to affect a physical property of the polymer such as solubility, glass transition temperature, lipophilicity, morphology creep, crystallinity, bulk modulus, viscosity, conductivity, refractive index or thermal stability. The chain ends can be deactivated in any appropriate fashion, for example, with an oxygen source or by nucleophiles. The polymer can be reacted with for example, $SO_3$, NaOR, or $NH_2R$, wherein R is an aliphatic or aromatic group. $SO_3$ can react selectively with the end group to deactivate propagation. NaOR and $NH_2R$ may react with the end group and the polymer chain indiscriminately. However, the use of these compounds in producing polymers makes these convenient choices. Hydride sources may also selectively react with the endgroup.

In one embodiment, a moiety is reacted with the cationic polymer end that contains a second functional group that can be used to link another desired moiety to the polymer. Non-limiting examples of second active functional groups include, but are not limited to (and protected as necessary) amines, imines, alkylsiloxysilane, hydroxyl, carboxylic acid, carboxylic acid chlorides, carboxylic acid anhydrides, amides, esters, sulfonic acid, sulfonic acid chlorides, phosphonic acid, phosphonic acid chloride, halogen or alkyl halides, alkynes, ethers, aldehydes, ketones, heteroaromatic compounds including pyridine, nitriles, amines, ammonium salts, and silanes.

In an alternative embodiment, a moiety can be added to the polymer that imparts specific biological properties to the polymer such as cationic charge (e.g., polylysine or other positive charge-bearing species, for tissue adherence), or provides a site for the attachment of a biologically active molecule, including but not limited to an antibody, antigen, protein, polysaccharide, nucleoprotein, lipoprotein, synthetic polypeptide, or a small molecule linked to a protein, steroid, nucleic acid, nucleotide, nucleoside, oligonucleotide (including antisense oligonucleotides), cDNA, nucleic acid, or gene.

In another embodiment, the active chains may be endcapped with a tris(organo)phosphoranimine having the formula $R'_3P=NSiR_3$. R' can be, independently, among other things alkyl, alkenyl, alkynyl, aryl, alkoxy, aryloxy. A specific example of a tris(organo)phosphoranimine is $(CF_3CH_2O)_3P=NSiMe_3$ where the presence of the $SiMe_3$ group permits reaction with the polymeric cation, while the absence of a chlorine unit at phosphorus results in termination. For example, when a polymerized solution of $Cl_3P=N-SiMe_3$, initiated with a 2% molar equivalent of $PCl_5$ in $CH_2Cl_2$, was treated with trace quantities of $(CF_3CH_2O)_3P=NSiMe_3$ at regular intervals during the polymerization, the growth of the polymeric cation was quenched as monitored $^{31}P$ NMR spectroscopy. GPC examination of the resultant polymers after chlorine replacement with $NaOCH_2CF_3$ showed a consistent range of molecular weights for the end-capped polymerization. (See, Table 3). Unfortunately, the presence of the terminal $-N=P(OCH_2CF_3)_3$ group in the end-capped polymer could not be confirmed from the $^{31}P$ NMR spectrum of an oligomeric sample of poly(dichlorophosphazene) synthesized from treatment of $Cl_3P=N-SiMe_3$ with a 20% molar equivalent of $PCl_5$. The resonance for the terminal $-N=P(OCH_2CF_3)_3$ species was perhaps concealed by resonances for the oligo(dichlorophosphazene) species. In a further effort to confirm the presence of such endcapping groups, an oligomeric sample of $[N=PCl_2]_n$, synthesized by treatment of $Cl_3P=N-SiMe_3$ with a 10% molar equivalent of $PCl_5$, was treated with $Me_2(CF_3CH_2O)P=NSiMe_3$. Examination of this endcapped species by $^{31}P$ NMR spectroscopy revealed the terminal $-N=PMe_2(OCH_2CF_3)$ species from a doublet resonance at 9.4 ppm. The $M_n$ of this endcapped oligomer was found to be $5.9\times10^3$ (PDI=1.05, by GPC) after macromolecular substitution with $NaOCH_2CF_3$.

TABLE 3

| | +HU[a] | | | |
|---|---|---|---|---|
| Time (h) | Cl3=N—SiMe₃/ [N=PCl₂] | $M_n \times 10^{-4}$ Found[a] | $M_n \times 10^{-4}$ Calculated[b] | PDI |
| 1.25 | 70/30 | 2.6 | — | 1.06 |
| 2.5 | 36/64 | 3.2 | — | 1.05 |
| 3.75 | 5/95 | 3.8 | — | 1.03 |
| 24 | 0/100 | 4.0 | 2.4 | 1.02 |

[a]All experiments were carried out with a monomer to initiator ratio of 50:1
[b]Calculated from the initial ratio of monomer to PCl₅ initiator Example 11

Activity of Growing Polyphosphazene Chain

The activity of the growing polymer chain of poly(dichlorophosphazene) was investigated. A solution of poly(dichlorophosphazene) in $CH_2Cl_2$ was prepared in which all of the phosphoranimine had been converted to polymer as determined by $^{31}P$ NMR spectroscopy. A portion of this was subjected to halogen replacement to yield a trifluoroethoxy-substituted polymer with an $M_w=1.1\times10^4$ with a PDI=1.04. A further addition of phosphoranimine to the remainder of the original (unsubstituted) solution resulted in the continued conversion of $Cl_3P=NSiMe_3$ to polymer over 48 hours. The GPC trace of the trifluoroethoxy-derivitized polymer from this solution showed the presence of polymer with a $M_w=9.2\times10^5$ with a PDI=1.71. Thus, it appears that the active chain ends can resume chain growth following the addition of more monomer. This opens up many possibilities for control over the chain length and coupling of the chain ends to other monomers or polymers.

VI. Block Copolymerization of Polyphosphazenes

The method of preparation of polyphosphazenes disclosed herein provides a route for the first time to a wide variety of phosphazene block copolymers. Using the prior art methods, the only known block copolymers were $[NP(OR_1)_2]_x[NP(OR_1)(OR_2)]_y$, wherein $R_1$ is halogenated alkoxy and $R_2$ is an aliphatic or aryl moiety. It is now possible to obtain block copolymers other than these limited polymers.

Block copolymers of polyphosphazenes can be prepared using at least three different methods. In a first embodiment, a block copolymer is prepared by the cationic polymerization of monomers initiated by the active end groups of the polyphosphazene. Any monomer or polymer capable of reacting with a cationic site can be used. Examples of monomers that react by cationic mechanisms include epoxides, oxiranes, episulfides, trioxanes, tetrahydrofurans, vinyl ethers, acrolein, and other olefins capable of cationic polymerization, such as 1-alkyl olefins (α-olefins), 1,1-dialkyl olefins, 1,3-dienes, styrene, a-methyl styrene, N-vinyl carbazole, N-vinyl pyrrolidone, and aldehydes and ketones. Additionally, other phosphazene monomers can be used to create phosphazene-phosphazene blocks. The active organic block can then be reacted with additional phosphoranimine monomer, that is the same as or different from that used in the first phosphazene polymer block. This procedure can be continued as long as desired using any variety of cationic organic and phosphoranimine monomers, or different phosphoranimine monomers without organic blocks. Blocks should be added prior to substitution since substitution can deactivate the chain ends.

In a second embodiment for the production of block copolymers of polyphosphazenes, functionalized compounds are reacted with the active polyphosphazene end that have a moiety that will initiate a reaction mechanism other than cationic polymerization, for example, anionic or radical initiation. Any initiator that can be attached to the end of a polymer chain and is incorporated into the second block can be used. For example, endcaps with bromophenyl moieties can be converted to an appropriate organometallic species, for example, Grignard or organolithium reagents, to initiate anionic polymerization of appropriate monomers. Alkene moieties can be used for metathesis reactions. Optionally, at an appropriate time, one can then react the anionic end with a monomer or polymer that has a group capable of initiating cationic polymerization to add another polyphosphazene block. Examples of these monomers include vinyl ether and butadiene. The monomer must undergo a living polymerization to have ABA block formation of phosphazene-organic-phosphazene in this manner. For example, the use of endcaps that contain haloalkyl or haloaryl moieties, for example, bromophenyl moieties, can be converted to an appropriate organometallic reagent, such as a grignard or organolithium reagent, to allow for the anionic polymerization of monomers that polymerize through anionic mechanisms, such styrene siloxanes, ethylene acrylates, methacrylates, acrylamide, methacrylamide, acrylonltrile, and methacrylonitrile. Optionally, at an appropriate time, one can then react the anionic end with a monomer or polymer that has a group capable of initiating cationic polymerization to add another polyphosphazene block. The use of pre-formed polymers with reactive endgroups which can be capped with phosphoranimines and converted to active $P=NP^+$ salts amino or hydroxyl terminated polymers can be used as templates for the synthesis of macroinitiators of the type, $PCl_6Cl_3P^+$—$N=PR_2$—Polymer-$R_2P=NPCl_3^+PCl_6^-$. Thus synthesis of multiblock copolymers is possible via growth from the prepolymer chain ends.

In a third embodiment for the preparation of block copolymers, initiators for the phosphazene polymerization can be included in other polymer systems. For example, an organic polymer with an $N=PR_3$ endgroup can be used to initiate phosphazene polymerization.

Example 12

Preparation of Organic Polymer/Polyphosphazene Block Copolymer

The commercially available polymeric bidentate amine $NH_2$—PEG-$NH_2$[where PEG=—$CH_2CH_2O(CH_2CH_2O)_n$—$CH_2CH_2$—, $M_n$=3400] was mixed with $(CF_3CH_2O)_2rP=NSiMe_3$ in the presence of $NEt_3$ to produce the phosphoranimine $NH(R_2P=NSiMe_3)$—$(CH_2CH_2O)_n$—$CH_2CH_2N(H)(R_2P=NSiMe_3)$. Subsequently, the phosphoranimine was reacted with two molar equivalents of $PCl_6$ at $-78°$ C. in $CH_2Cl_2$ which resulted in the formation of the macroinitiator $NH(R_2P=NPCl_3^+)$ $PCl_6^-$—$(CH_2CH_2O)_n$—$CH_2CH_2N(H)[R_2P=NPCl_3^+]PCl_6$. This macroinitiator was then treated with a thirty fold excess of $Cl_3P=NSiMe_3$ and after 3 h at 25° C. examination of the reaction mixture by 31 P NMR spectroscopy revealed the complete conversion to a new form of poly(dichlorophosphazene), $NHR_2P$—$(N=PC_2)_m$—$(CH_2CH_2O)_n$—$CH_2CH_2N(H)Cl_2P[N=PR_2]_m$. This product was treated with an excess of a sodium trifluoroethoxide in dioxane solution to replace the chlorine atoms by trifluoroethoxy groups and generate the hydrolytically stable block copolymer $NHR_2P$—$(N=PR_2)$—$(CH_2CH_2O)_n$—$CH_2CH_2N(H)R_2P[N=PR_2]_m$ with $R=OCH_2CF_3$. Analysis of this block copolymer by gel permeation chromatography (GPC) in THF indicated that it possessed an $M_n$ of $1.5\times10^4$ and a polydispersity index of 1.16 versus polystyrene standards.

VII. Triarmed-Star Polyphosphazenes

Example 13

Synthesis of the Triarmed-Star Polyphosphazene $N\{CH_2CH_2NH(CF_3CH_2O)_2P$—$[N=P(OCH_2CF_3)_2]_n\}_3$ Phosphoranimines such as can readily undergo substitution reactions in the presence of alkoxides or amines, to produce $(CF_3CH_2O)_2RP=NSiMe_3$ species (R=RO— or RNH—). With this in mind, the tridentate primary amine $N(CH_2CH_2NH_2)_3$ was mixed with $(CF_3CH_2O)_2BrP=NSiMe_3$, in the presence of $NEt_3$, to produce the trifunctional phosphoranimine $N\{CH_2CH_2NH(CF_3CH_2O)_2P=NSiMe_3\}3$. Subsequent reaction of $N\{CH_2CH_2NH(CF_3CH_2O)_2P=NSiMe_3\}_3$ with six molar equivalents of $PCl_5$ at $-78°$ C. in $CH_2Cl_2$ resulted in the formation of the trifunctional cationic species $[N\{CH_2CH_2NH(CF_3CH_2O)_2P=N$—$PCl_3^+\}_3][PCl_6^-]_3$. This species was then treated with a thirty-fold excess (per reactive site) of $Cl_3P=NSiMe_3$ in $CH_2Cl_2$. After 3 h at 25° C., examination of the reaction mixture by $^{31}P$ NMR spectroscopy revealed the complete conversion of $Cl_3P=N$—$SiMe_3$ a new form of poly(dichlorophosphazene), $(N=PCl_2)_n$, based on a characteristic resonance at $-17$ ppm with loss of the doublet resonances for $[N\{CH_2CH_2NH(CF_3CH_2O)_2P=N$—$PCl_3\}3][PC_6]3$. Also detected was a doublet resonance at ca. 8.2 ppm, as well as triplet resonances at $-14.5$, and $-15.5$ ppm, consistent with the presence of the star-polymer $N\{CH_2CH_2NH(CF_3CH_2O)_2P=N$—$PCl_2N=PC_2[N=PCl_2]_n\}_3$. Integration of the $^{31}P$ NMR resonances associated with the star polymer were consistent with theoretical values based on the initial reactant ratio. This product was treated with an excess of sodium trifluoroethoxide to replace the chlorine atoms by trifluoroethoxy groups and generate the hydrolytically stable star-polymer $N\{CH_2CH_2NH(CF_3CH_2O)_2P$—$[N=P(OCH_2CF_3)_2]_n\}_3$. Analysis of this polymer by gel permeation chromatography (GPC) indicated that it possessed an $M_n$ of $2.1\times10^4$ and a polydispersity index of 1.03 versus polystyrene standards. The molecular weights of these star-polymers can be controlled by variation of monomer:initiator ratios. (See, Table 4). End-group analysis by $^{31}P$ NMR spectroscopy was also used to provide molecular weight estimates in cases where the end-group unit [—N—P$(OCH_2CF_3)_2$] was detectable.

TABLE 4

| M:I/ Reactive Site | Reaction Time (h) | $M_n$ Found[a] | $M_n$ Found[b] | $M_n$ Calculated[c] | PDI |
|---|---|---|---|---|---|
| 10:1 | 0.66 | 12,630 | 9,146 | 9,146 | 1.05 |
| 15:1 | 1 | 16,987 | 12,971 | 12,971 | 1.02 |
| 30:1 | 3 | 20,610 | 23,726 | 23,726 | 1.03 |

TABLE 4-continued

| M:I/ Reactive Site | Reaction Time (h) | $M_n$ Found[a] | $M_n$ Found[b] | $M_n$ Calculated[c] | PDI |
|---|---|---|---|---|---|
| 50:1 | 6 | 35,319 | NA | 38,306 | 1.03 |
| 100:1 | 14 | 41,606 | NA | 74,756 | 1.36 |

[a]Molecular weights by GPC following replacement of Cl by $NaOCH_2CF_3$
[b]Molecular weights by end group analysis using $^{31}P$ NMR spectroscopy
[c]Calculated at 100% conversion Preliminary comparisons of the physical properties of low molecular weight samples of $N\{CH_2CH_2NH(CF_3CH_2O)_2P—[N=P(OCH_2CF_3)_2]_n\}_3$ with the linear analogue $[N=P(OCH_2CF_3)_2]_n$ of comparable molecular weight ($1.2 \times 10^4$), revealed that, while the linear polymer is a crystalline white fibrous material which readily forms films, the triarmed star polymer is a pale yellow, viscous gum. The corresponding star and linear polymers with molecular weights higher than $1.7 \times 10^4$ show similar physical characteristics. In addition, GPC chromatograms for $N\{CH_2CH_2NH(CF_3CH_2O)_2P—[N=P(OCH_2CF_3)_2]_n\}_3$ with $M_n$ above $2.1 \times 10^4$ appear to underestimate the molecular weight and provide indirect evidence of its branched nature. Due to the well-known fire-retardant properties of polyphosphazenes, these controlled molecular weight star polymers may prove useful as additives to flammable organic polymers.

Example 14

General Schemes for Synthesis of Polyphosphazenes Having Controlled Molecular Weights and Polydispersity The present Example describes generalized schemes for producing polyphosphazenes compositions having controlled molecular weight and polydispersity based on use and routine adaptation of methods known in the art. (See e.g., Allcock H. R., et al, "'Living' Cationic Polymerization of Phosphoranimines as an Ambient Temperature Route to Polyphosphazenes with Controlled Molecular Weights," Macromolecules, 29:24, pp. 7740-7747, 18 Nov. 1996; Wang B., "Development of a One-Pot in Situ Synthesis of Poly(dichlorophosphazene) from $PCl_3$," Macromolecules, 38(2), pp. 643-645, 24 Dec. 2005; Allcock, H. R., "Synthesis, Structures, and Emerging Uses for Poly(organophosphazenes)," Polyphosphazenes in Biomedicine, Engineering, and Pioneering Synthesis, Ch. 1, pp. 3-26, 2 Aug. 2018; and Gabino A., et al., "Designed Synthesis of Polyphosphazene Block Copolymers for Self-Assembly," Polyphosphazenes in Biomedicine, Engineering, and Pioneering Synthesis, Ch. 10, pp. 211-240, 2 Aug. 2018).

The art is aware of various methods for synthesizing poly(dichlorophosphazene) at ambient temperatures as referenced in this Example. Generally, these methods involve the initiation of $Cl_3P=NSiMe_3$ with small amounts of $PCl_5$ in $CH_2Cl_2$ to yield poly(dichlorophosphazene), $(NPCl_2)_n$, with controlled (narrow) polydispersity. In these types of methods, $PBr_5$, $SbCl_5$, and $Ph_3C[PF_6]$ are effective initiators in $CH_2Cl_2$ at room temperature. The molecular weight of poly(dichlorophosphazene) can be controlled by altering the ratio of monomer to initiator. Polymer chains are active after chain propagation since further addition of monomer results in the formation of higher molecular weight polymer(s). $^1H$ and $^{31}P$ NMR spectral analysis of these reactions can be used to show polymerization follows first-order reaction kinetics with respect to monomer concentration. Active polymer chains can be quenched or end-capped by the addition of trace quantities of $Me_2(CF_3CH_2O)P=NSiMe_3$ or $(CF_3CH_2O)_3P=NSiMe_3$.

Allcock et al., 1996, supra, provides one generally applicable reaction schematic, as shown below.

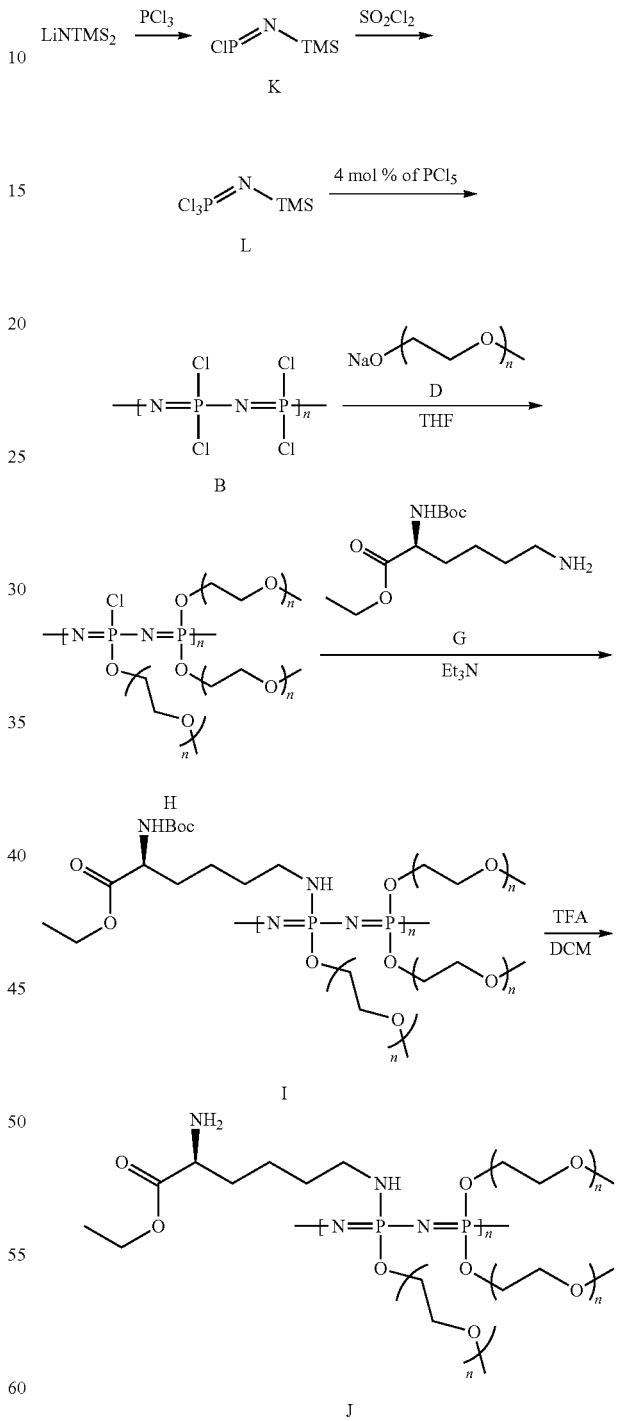

Target molecular weights of product "J" (See, FIG. 1) can be controlled by routine experimentation and method design. Finally, purification and quantification steps are understood and routinely available to the skilled artisan.

Example 15

Synthesis of Polyphosphazene-Paclitaxel Conjugate [NP(MPEG550)$_3$(Lys-OEt)(AA)(PTX)]$_n$ This Example provides a method for synthesizing suitable polyphosphazene and subsequently conjugating thereto a drug substance of interest (i.e., Paclitaxel, "PTX").

Synthesis of polyphosphazene carrier polymer [NP(MPEG550)$_3$(Lys-OEt)]$_n$

A. Preparation of Cl$_3$P=NSiMe$_3$

LiN(SiMe$_3$)$_2$ (4.94 g, 29.5 mmol) was dissolved in pentane (100 mL) and the solution was cooled to 0° C. using an ice-acetone bath. PCl$_3$ (3.98 g, 29 mmol) was then added dropwise over 10 min. The resulting mixture was stirred at 0° C. for 30 min giving a white suspension. SO$_2$Cl$_2$ (4.18 g, 31 mmol) was then added dropwise over 10 min to the suspension at 0° C. The reaction was allowed to proceed for 30 min at 0° C. The mixture was then filtered through Celite (dried at ~120° C. for >48 h prior to use), which was then washed with pentane (2×20 mL). The volatiles from the resulting pale yellow filtrate were removed under vacuum (20 mm Hg, 0° C.) to Cl$_3$P=NSiMe$_3$ (5.2 g, 78%) as give pale yellow liquid, which was sufficiently pure for use in the next step.

B. Preparation of Polyphosphazene Carrier Polymer [NP(MPEG550)$_3$(Lys-OEt)]$_n$ Poly(dichlorophosphazene) was prepared from Cl$_3$P=NSiMe$_3$ in the presence of PCl$_5$ as a catalyst according to the method of Allcock et al. (Allcock H. R., et al., 18 Nov. 1996, infra). A typical synthetic procedure follows: a solution of PCl$_5$ (74 mg, 0.356 mmol) in degassed CH$_2$Cl$_2$ (20 mL) was placed in a 50 mL RBF under nitrogen atmosphere and stirred with use of a magnetic stirrer. A solution of Cl$_3$P=NSiMe$_3$ (4 g, 17.81 mmol) in degassed CH$_2$Cl$_2$ (40 mL) was then added to the flask under stirring. The reaction mixture was monitored by $^1$H-NMR spectroscopy. After 4 h, Cl$_3$P=NSiMe$_3$ was completely converted to the polymer. The volatiles were removed under reduced pressure to obtain poly(dichlorophosphazene) ([NPCl$_2$]$_n$) (2.0 g).

The sodium salt of MPEG550 was prepared by reaction of MPEG550 (14.22 g, 25.85 mmol) with an excess amount of sodium metal (1.2 g, 52.17 mmol) in dry toluene at refluxing temperature for 12 h. After the resultant solution was filtered to remove excess sodium metal, the filtrate was dropped slowly into a solution of poly(dichlorophosphazene) ([NPCl$_2$]$_n$) (2.0 g, 17.26 mmol) dissolved in dry THF (100 mL) at −5° C. to 0° C. The reaction mixture was stirred for 2 h at −5° C. to 0° C. and further stirred at room temperature for 16-18 h to yield PEGylated polyphosphazene.

Boc-lysine ethyl ester (Na-Boc-Lys-OEt, 3.7 g, 13.5 mmol) was dissolved in dry chloroform (100 mL) and neutralized with dry triethylamine (Et$_3$N, 13.6 g, 134.4 mmol). This solution was added slowly to the above prepared PEGylated polymer solution and allowed to react at room temperature for 24 h. The reaction mixture was filtered to remove the by-products (Et$_3$N·HCl or NaCl salts), and the filtrate was concentrated under vacuum to provide the polymeric phosphazene as brown colored thick oil.

The '-Boc protecting group from the polymeric phosphazene was removed by dissolving the above residue in a mixed solution of CH$_2$Cl$_2$ (20 mL) and TFA (20 mL). The reaction mixture was stirred at room temperature for 6 h, and the solvent was evaporated under vacuum. The product was neutralized with NaHCO$_3$ solution and dialyzed in water using regenerated cellulose membranes (MWCO: 3.5 kDa) for 24 h.

The dialyzed solution was freeze dried to obtain the pure carrier polymer [NP(MPEG550)$_3$(Lys-OEt)]$_n$, which was fractionated in distilled water using cellulose membranes with molecular weight cut-off at 25 and 100 kDa. Yield: 4.0 g (MWCO: 25 kDa); 1.0 g (MWCO: 100 kDa).

Example 16

Intravenous Toxicity Study

The objective of this study was to determine the maximum tolerated dose in test animals following a single parenteral administration, in this case an intravenous (IV) injection, of the drug delivery compositions to Sprague-Dawley rats followed by a 7-day observation period.

Test Drug Delivery Composition

In this Example, drug delivery compositions were optimized to carry and deliver the active chemotherapeutic agent Paclitaxel (PTX at about 5%). (See, Table 5 infra). Briefly, under sterile conditions in a laminar flow cabinet sterile water for formation and injection purposes was added to the appropriate amount of drug deliver composition to provide concentrations of 350, 817, 1167, and 1750 mg/mL. The diluted drug deliver compositions were stirred, mixed, or vortexed as necessary to achieve sufficient distribution. The prepared drug deliver compositions were stored protect from light at ambient temperature. The final formulation for each concentration was passed through a 0.2 μm filter prior to administration. The target volume prepared for each dose was 1.55 mL. The actual volume dispensed post-filtering was recorded. Final formulations for administration can be used up to 4 hours after preparation.

Animal Subjects

Subjects in this Example consisted of age appropriate to weight intact male Sprague-Dawley rats. Various commercial sources of Sprague-Dawley rats are acceptable for supply of Subject animals. Maximum Subject animal weight at initiation of the administrations was 330 gm while minimum weight was 260 gm. Subject animals were housed, feed, provided watered ad libitum, and observed according to standard animal husbandry protocols. Subject animals were excluded for any observable disease or injury that could affect study outcome.

Subject Animals were observed BID from the day they were received from the vendor to being euthanatized for their physical and behavioral attributes such as, but not limited to, the following: 1) weight loss (e.g., more than 20% of bodyweight from pre-dosing values); 2) moribund state (e.g., depression, complete anorexia and hypothermia, comatose/pale/cold to the touch for an extended period of time); 3) inability or extreme reluctance to stand (e.g., persisting for 24 hr); 4) CNS disorders (e.g., persistent head tilt, incoordination, ataxia, tremors, spasticity, seizures, circling, or paresis for longer than 1 h.); 5) uncontrollable pain/distress; 6) signs of pain and/or distress for an extended period of time; 7) miscellaneous conditions (e.g., diarrhea, constipation, or vomiting, if prolonged and leading to emaciation and/or debilitation, prolonged or intense diuresis leading to severe dehydration); and 8) complications that may be related to a study specific activity (e.g., catheter dislodgement, incision bleeding, etc.).

The attending veterinarian is alerted if any significant abnormal clinical observations are observed and the animal treated as deemed necessary by the veterinarian to alleviate pain and/or distress, which may include euthanasia.

Test Drug Delivery Composition Administrations

Briefly, as per Table 5, Subject 1 received a 1750 mg/kg (dose volume 5 mL/kg) by slow (1 mL/min) bolus IV injection on Day 0 of the drug delivery composition. Subject 2 received a 4083 mg/kg (dose volume 5 mL/kg) by slow (1 mL/min) bolus IV injection on Day 0 of the drug delivery composition approximately 1 hour after observing the previously dosed Subject 1. Subject 3 received a 5833 mg/kg (dose volume 5 mL/kg) by slow (1 mL/min) bolus IV injection on Day 0 of the drug delivery composition approximately 1 hour after observing the previously dosed Subject 2. Finally, Subject 4 received a 8750 mg/kg (dose volume 5 mL/kg) by slow (1 mL/min) bolus IV injection on Day 0 of the drug delivery composition approximately 1 hour after observing the previously dosed Subject 3. All subject animals were observed for 7-days following administration of the drug delivery composition. Dosing was stopped if adverse clinical events were noted following administration of the active drug delivery composition. On Day 7, animals were humanely euthanized and necropsies were performed.

TABLE 5

Dose Levels

| Group | Number of Animals | Treatment PTX Mg/m2 | Treatment PTX Mg/kg | Treatment PETTAX121 Mg/kg | Dose Volume mL/kg | Concentration of PETTAX-121 Mg/mL |
|---|---|---|---|---|---|---|
| 1 | 1 | 525 | 87.5 | 1750 | 5 | 350 |
| 2 | 1 | 1225 | 204.2 | 4083 | 5 | 817 |
| 3 | 1 | 1750 | 291.7 | 5833 | 5 | 1167 |
| 4 | 1 | 2625 | 437.5 | 8750 | 5 | 1750 |

Clinical Observations

Animal Subjects were observed BID from the day they were received from the vendor until euthanatized for physical and behavioral attributes such as, but not limited to, as mentioned above on the post administration schedule set for in Table 6 below.

TABLE 6

Post-Administration Clinical Observations

| Activity | Procedure Type(s) Included: Subject Animal Group | Time Point | Relative Time Post Procedure | Freq. | Method |
|---|---|---|---|---|---|
| Morbidity and Mortality Observations | All | Not Applicable | Day 0 through termination | BID | Per Protocol |
| Clinical Observations | All | Day 0 (1 Hr. post admin.) | 1 hr. (±10 min.) | 1x | Per Protocol |
| Clinical Observations | All | Day 0 (2 Hr. post admin.) | 2 hr. (±10 min.) | 1x | Per Protocol |
| Clinical Observations | All | Day 0 (3 Hr. post admin.) | 3 hr. (±10 min.) | 1x | Per Protocol |
| Clinical Observations | All | Day 0 (4 Hr. post admin.) | 4 hr. (±10 min.) | 1x | Per Protocol |
| Clinical Observations | All | Not Applicable | Day 1 through termination | BID | Per Protocol |
| Body Weight | All | Not Applicable | Day 3 | 1x | Per Protocol |

Clinical Results

Subject Animals in Groups 1-3 tolerated their respective administration well with no observed adverse reactions or clinically significant observations recorded during the entirety of the study. There were no significant physical changes noted in the Animals of Groups 1-3. The animal in Group 4 was euthanized 20 hours after administration due to observed morbidity.

Exemplary Therapeutic and Chemotherapeutic Agents

Preferred embodiments of the present polymeric drug carrier and delivery systems are formulated and optimized to delivery one or more anticancer or antitumor drug agents or substances such as, but not limited to: Abemaciclib, Abiraterone Acetate, Acalabrutinib, Adriamycin, Afatinib Dimaleate, Afinitor (Everolimus), Aldara (Imiquimod), Aldesleukin, Alecensa (Alectinib), Alectinib, Alimta (Pemetrexed Disodium), Aliqopa, (Copanlisib Hydrochloride), Aloxi (Palonosetron Hydrochloride), Alpelisib, Alunbrig (Brigatinib), Ameluz (Aminolevulinic Acid Hydrochloride), Amifostine, Aminolevulinic acid hydrochloride, Anastrozole, Apalutamide, Aprepitant, Aredia (Pamidronate Disodium), Arimidex (Anastrozole), Aromasin (Exemestane), Arranon (Nelarabine), Arsenic Trioxide, Asparaginase *Erwinia Chrysanthemi*, Asparlas, (Calaspargase Pegol-Mknl), Axicabtagene Ciloleucel, Axitinib, Azacitidine, Azedra (Iobenguane I 131), Balversa (Erdafitinib), Beleodaq (Belinostat), Belinostat, Bendamustine Hydrochloride, Bendeka, (Bendamustine Hydrochloride), Bexarotene, Bicalutamide, Bicnu (Carmustine), Binimetinib, Bleomycin Sulfate, Bortezomib, Bosulif (Bosutinib), Bosutinib, Braftovi (Encorafenib), Brigatinib, Bumel, Busulfan, Cabazitaxel, Cabometyx (Cabozantinib-S-Malate), Cabozantinib-S-Malate, Calaspargase Pegol-Mknl, Calquence (Acalabrutinib), Camptosar (Irinotecan Hydrochloride), Capecitabine, Carboplatin, Carfilzomib, Carmustine, Casodex (Bicalutamide), Ceritinib, Cerubidine (Daunorubicin Hydrochloride), Chlorambucil, Cisplatin, Cladribine, Clofarabine, Clolar (Clofarabine), Cobimetinib, Cometriq, (Cabozantinib-S-Malate), Copanlisib Hydrochloride, Copiktra (Duvelisib), Cosmegen (Dactinomycin), Cotellic (Cobimetinib), Crizotinib, Cyclophosphamide, Cytarabine, Dabrafenib Mesylate, Dacarbazine, Dacogen (Decitabine), Dacomitinib, Dactinomycin, Darolutamide, Dasatinib, Daunorubicin Hydrochloride, Daurismo (Glasdegib Maleate), Decitabine, Defibrotide Sodium, Defitelio (Defibrotide Sodium), Degarelix, Denileukin Diftitox, Dexamethasone, Dexrazoxane Hydrochloride, Doxorubicin Hydrochloride, Duvelisib, Eligard (Leuprolide Acetate), Elitek (Rasburicase), Ellence (Epirubicin Hydrochloride), Eloxatin (Oxaliplatin), Eltrombopag Olamine, Elzonris (Tagraxofusp-Erzs), Emend (Aprepitant), Enasidenib Mesylate, Encorafenib, Enzalutamide, Epirubicin Hydrochloride, Erdafitinib, Eribulin Mesylate, Erivedge (Vismodegib), Erleada (Apalutamide), Erlotinib Hydrochloride, Erwinaze (Asparaginase *Erwinia Chrysanthemi*), Ethyol (Amifostine), Etopophos (Etoposide Phosphate), Etoposide, Etoposide Phosphate, Everolimus, Evista (Raloxifene Hydrochloride), Evomela (Melphalan Hydrochloride), Exemestane, Fareston (Toremifene), Farydak (Panobinostat), Faslodex (Fulvestrant), Fedratinib Hydrochloride, Femara (Letrozole), Filgrastim, Firmagon (Degarelix), Fludarabine Phosphate, Flutamide, Folotyn (Pralatrexate), Fostamatinib Disodium, Fulvestrant, Fusilev (Leucovorin Calcium), Gefitinib, Gemcitabine Hydrochloride, Gemzar (Gemcitabine Hydrochloride), Gilotrif (Afatinib Dimaleate), Gilteritinib Fumarate, Glasdegib Maleate, Gleevec (Imatinib Mesylate), Glucarpidase, Goserelin Acetate, Granisetron, Granisetron Hydrochloride, Granix (Filgrastim), Halaven (Eribulin Mesylate), Hemangeol (Propranolol Hydrochloride), Hycamtin (Topotecan Hydrochloride), Hydrea (Hydroxyurea), Hydroxyurea, Ibrance (Palbociclib), Ibrutinib, Iclusig (Ponatinib Hydrochloride), Idamycin PFS (Idarubicin Hydrochloride), Idarubicin Hydrochloride, Idelalisib, Idhifa (Enasidenib Mesylate), Ifex (Ifosfamide), Ifosfamide, Imatinib Mesylate, Imbruvica (Ibrutinib), Imiquimod, Imlygic (Talimogene Laherparepvec), Inlyta (Axitinib), Inrebic (Fedratinib Hydrochloride), Iobenguane I 131, Iressa (Gefitinib), Irinotecan Hydrochloride, Istodax (Romidepsin), Ivosidenib, Ixabepilone, Ixazomib Citrate, Ixempra (Ixabepilone), Jakafi (Ruxolitinib Phosphate), Jevtana (Cabazitaxel), Kepivance (Palifermin), Kisqali (Ribociclib), Kymriah (Tisagenlecleucel), Kyprolis (Carfilzomib), Lanreotide Acetate, Lapatinib Ditosylate, Larotrectinib Sulfate, Lenalidomide, Lenvatinib Mesylate, Lenvima (Lenvatinib Mesylate), Letrozole, Leucovorin Calcium, Leukeran (Chlorambucil), Leuprolide Acetate, Levulan Kerastik (Aminolevulinic Acid Hydrochloride), Lomustine, Lonsurf (Trifluridine And Tipiracil Hydrochloride), Lorbrena (Lorlatinib), Lorlatinib, Lutathera (Lutetium Lu 177-Dotatate), Lutetium (Lu 177-Dotatate), Lynparza (Olaparib), Matulane (Procarbazine Hydrochloride), Mechlorethamine Hydrochloride, Megestrol Acetate, Mekinist (Trametinib), Mektovi (Binimetinib), Melphalan, Melphalan Hydrochloride, Mercaptopurine, Mesna, Methotrexate, Methylnaltrexone Bromide, Midostaurin, Mitomycin C, Mitoxantrone Hydrochloride, Mozobil (Plerixafor), Mustargen (Mechlorethamine Hydrochloride), Myleran (Busulfan), Navelbine, (Vinorelbine Tartrate), Nelarabine, Neratinib Maleate, Nerlynx (Neratinib Maleate), Neulasta, (Pegfilgrastim), Neupogen (Filgrastim), Nexavar (Sorafenib Tosylate), Nilandron (Nilutamide), Nilotinib, Nilutamide, Ninlaro (Ixazomib Citrate), Niraparib Tosylate Monohydrate, Nplate (Romiplostim), Nubeqa (Darolutamide), Odomzo (Sonidegib), Olaparib, Omacetaxine Mepesuccinate, Oncaspar (Pegaspargase), Ondansetron Hydrochloride, Ontak (Denileukin Diftitox), Osimertinib Mesylate, Oxaliplatin, Paclitaxel ("PTX") (Taxol) (5β,20-Epoxy-1,2α,4,7 (β,10β,13α-hexahydroxytaxl 1-en-9-one 4, 10-diacetate 2-benzoate 13-ester with (2R,3S)—N-benzoyl-3-phenylisoserine), Palbociclib, Palifermin, Palonosetron Hydrochloride, Panobinostat, Pazopanib Hydrochloride, Pegaspargase, Pegfilgrastim, Pemetrexed Disodium, Piqray (Alpelisib), Plerixafor, Pomalidomide, Pomalyst (Pomalidomide), Ponatinib Hydrochloride, Pralatrexate, Prednisone, Procarbazine Hydrochloride, Proleukin (Aldesleukin), Promacta (Eltrombopag Olamine), Propranolol Hydrochloride, Provenge (Sipuleucel-T), Purinethol (Mercaptopurine), Purixan (Mercaptopurine), Radium 223 Dichloride, Raloxifene Hydrochloride, Rasburicase, Regorafenib, Relistor (Methylnaltrexone Bromide), Revlimid (Lenalidomide), Rheumatrex (Methotrexate), Ribociclib, Rolapitant Hydrochloride, Romidepsin, Romiplostim, Rubidomycin (Daunorubicin Hydrochloride), Rubraca (Rucaparib Camsylate), Rucaparib Camsylate, Ruxolitinib Phosphate, Rydapt (Midostaurin), Sancuso (Granisetron), Selinexor, Sipuleucel-T, Sonidegib, Sorafenib Tosylate, Sprycel (Dasatinib), Stivarga (Regorafenib), Sunitinib Malate, Sustol (Granisetron), Sutent (Sunitinib Malate), Synribo (Omacetaxine Mepesuccinate), Tabloid (Thioguanine), Tafinlar (Dabrafenib Mesylate), Tagraxofusp-Erzs, Tagrisso (Osimertinib Mesylate), Talazoparib Tosylate, Talimogene Laherparepvec, Talzenna (Talazoparib Tosylate), Tamoxifen Citrate, Tarceva (Erlotinib Hydrochloride), Targretin (Bexarotene), Tasigna (Nilotinib), Tavalisse (Fostamatinib Disodium), Temodar (Temozolomide), Temozolomide, Temsirolimus, Thalidomide, Thalomid (Thalidomide), Thioguanine, Thiotepa, Tibsovo (Ivosidenib), Tisagenlecleucel, Topotecan Hydrochloride, Toremifene, Torisel (Temsirolimus), Totect (Dexrazoxane Hydrochloride), Trabectedin, Trametinib, Treanda (Bendamustine Hydrochloride), Trexall (Methotrexate), Trifluridine and Tipiracil Hydrochloride, Trisenox (Arsenic Trioxide), Tykerb (Lapatinib Ditosylate), Uridine Triacetate, Valrubicin, Valstar (Valrubicin), Vandetanib, Varubi (Rolapitant Hydrochloride), Veip, Velcade (Bortezomib), Vemurafenib, Venclexta (Venetoclax), Venetoclax, Verzenio (Abemaciclib), Vidaza (Azacitidine), Vinblastine Sulfate, Vincristine Sulfate, Vinorelbine Tartrate, Vismodegib, Vistogard (Uridine Triacetate), Vitrakvi (Larotrectinib Sulfate), Vizimpro (Dacomitinib), Voraxaze (Glucarpidase), Vorinostat, Votrient (Pazopanib Hydrochloride), Xalkori (Crizotinib), Xeloda (Capecitabine), Xofigo (Radium 223 Dichloride), Xospata (Gilteritinib Fumarate), Xpovio (Selinexor), Xtandi (Enzalutamide), Yescarta (Axicabtagene Ciloleucel), Yondelis (Trabectedin), Zaltrap (Ziv-Aflibercept), Zarxio (Filgrastim), Zejula (Niraparib Tosylate Monohydrate), Zelboraf (Vemurafenib), Zinecard (Dexrazoxane Hydrochloride), Ziv-Aflibercept, Zofran (Ondansetron Hydrochloride), Zoladex (Goserelin Acetate), Zoledronic Acid, Zolinza (Vorinostat), Zometa (Zoledronic Acid), Zydelig (Idelalisib), Zykadia (Ceritinib), and Zytiga (Abiraterone Acetate), and the like.

Various embodiments of the compositions of the present invention are formulated and optimized for treating, ameliorating, or retarding the metastasis thereof regarding a particular type of tumor or cancer, or a tumor or cancer of a particular organ, tissues, or structure, including, but not limited to: Acute Lymphoblastic Leukemia (ALL), Acute Myeloid Leukemia (AML), Adrenocortical Carcinoma, AIDS-Related Cancers (e.g., Kaposi Sarcoma (Soft Tissue Sarcoma), AIDS-Related Lymphomas, Anal Cancer, Appendix Cancer and Gastrointestinal Carcinoid Tumors, Astrocytomas, Atypical Teratoid/Rhabdoid Tumor, Basal Cell Carcinoma of the Skin, Bile Duct Cancer (e.g., Cholangiocarcinoma), Bladder Cancer, Bone Cancer (e.g., Ewing Sarcoma and Osteosarcoma and Malignant Fibrous Histiocytoma), Brain Tumors, Breast Cancer (e.g., Ductal Carcinoma in situ), Bronchial Tumors, Burkitt Lymphoma, Carcinoid Tumors, Carcinoma of Unknown Primary, Cardiac Tumors, Central Nervous System Tumors, Medulloblastoma and other CNS Embryonal Tumors, Germ Cell Tumor, Primary CNS Lymphoma, Cervical Cancer, Chordoma, Chronic Lymphocytic Leukemia (CLL), Chronic Myelogenous Leukemia (CML), Chronic Myeloproliferative Neoplasms, Colorectal Cancer, Craniopharyngioma, Cutaneous T-Cell Lymphoma (e.g., Mycosis Fungoides and Sézary Syndrome), Embryonal Tumors (e.g., Medulloblastoma), Endometrial Cancer (Uterine Cancer), Ependymoma, Esophageal Cancer, Esthesioneuroblastoma, Extracranial Germ Cell Tumor, Extragonadal Germ Cell Tumor, Eye Cancer (e.g., Intraocular Melanoma, Retinoblastoma), Fallopian Tube Cancer, Fibrous Histiocytoma of Bone, Malignant, and Osteosarcoma, Gallbladder Cancer, Gastric (Stomach) Cancer, Gastrointestinal Carcinoid Tumor, Gastrointestinal Stromal Tumors (GIST) (Soft Tissue Sarcoma), Ovarian Germ Cell Tumors, Testicular Cancer, Gestational Trophoblastic Disease, Hairy Cell Leukemia, Laryngeal Cancer, Hepatocellular (Liver) Cancer, Histiocytosis, Langerhans Cell, Hodgkin Lymphoma, Hypopharyngeal Cancer, Islet Cell Tumors, Pancreatic Neuroendocrine Tumors, Kidney (Renal Cell) Cancer, Langerhans Cell Histiocytosis, Lip and Oral Cavity and mouth Cancer, Liver Cancer, Non-Small Cell and Small Cell Lung Cancer, Malignant Fibrous Histiocytoma of Bone and Osteosarcoma, Melanoma, Merkel Cell Carcinoma, Malignant Mesothelioma, Metastatic Cancer, Occult Primary Metastatic Squamous Neck Cancer, Midline Tract Carcinoma, Multiple Endocrine Neoplasia Syndromes, Multiple Myeloma/Plasma Cell Neoplasms, Mycosis Fungoides, Myelodysplastic Syndromes, Myelodysplastic/Myeloproliferative Neoplasms, Chronic Myelogenous Leukemia (CML), Acute Myeloid Leukemia (AML), Chronic Myeloproliferative Neoplasms, Nasal Cavity and Paranasal Sinus Cancer, Nasopharyngeal Cancer, Neuroblastoma, Non-Hodgkin Lymphoma, Non-Small Cell Lung Cancer, Oropharyngeal Cancer, Osteosarcoma and Malignant Fibrous Histiocytoma, Pancreatic Cancer, Pancreatic Neuroendocrine Tumors, Papillomatosis, Paraganglioma, Parathyroid Cancer, Penile Cancer, Pheochromocytoma, Pituitary Tumor, Plasma Cell Neoplasm/Multiple Myeloma, Pleuropulmonary Blastoma, Prostate Cancer, Rectal Cancer, Rhabdomyosarcoma, Salivary Gland Cancer, Sarcoma, Ewing Sarcoma, Kaposi Sarcoma, Osteosarcoma, Soft Tissue Sarcoma, Uterine Sarcoma, Sezary Syndrome, Small Intestine Cancer, Squamous Cell Carcinoma of the Skin, Occult Primary Squamous Neck Cancer, T-Cell Lymphoma, Cutaneous (e.g., Mycosis Fungoides and Sezary Syndrome), Testicular Cancer, Thymoma and Thymic Carcinoma, Thyroid Cancer, Urethral Cancer, Uterine Sarcoma, Vaginal Cancer, Vulvar Cancer, Vascular Tumors, and Wilms Tumor, and the like.

Exemplary Formulation, Dosing, and Administration Methods

The practice of the present invention will employ, unless otherwise indicated, conventional techniques of preparing pharmaceutical formulations as well as administration and dosing techniques which are well known in the art. Generally speaking, final administrable formulations of the drug delivery systems and compositions of the present invention may optionally be prepared by means standard in the art. A number of standard text are known in the art regarding preparation and formulation considerations. (See e.g., Remington's Pharmaceutical Sciences).

In certain embodiments, the drug delivery systems and compositions of the present disclosure are provided as sterile and, optionally, preservative-free formulations. In other embodiments the drug delivery systems and compositions are sterile, optionally preservative-free, and formulated in a single-use or unit-dose formats. In still further embodiments the sterile formulations contain one or more preservatives, stabilizers, sugars, or sugar alcohols.

The methods and drug delivery systems and compositions of the present invention provide treatments for cancer and other proliferative diseases in a subject in order to confer a medicinal or therapeutic benefit in the subject by the administration of an effective dose of the one or more of compositions described herein. Methods of administering the compounds of the invention may be by metered dose or by one or more controlled release devices. The compositions may be in unit dosage forms suitable for single administration of precise dosages.

In some embodiments, the concentration of one or more of the active drug or therapeutic compounds provided in the drug delivery systems and compositions of the present invention is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v.

In yet some other embodiments, the concentration of one or more of the active drug or therapeutic compounds provided in the drug delivery systems and compositions of the present invention is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v.

In still some other embodiments, the concentration of one or more of the active drug or therapeutic compounds provided in the drug delivery systems and compositions of the present invention is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v.

In some embodiments, the concentration of one or more of the active drug or therapeutic compounds provided in the drug delivery systems and compositions of the present invention is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some other embodiments, the amount of one or more of the active drug or therapeutic compounds provided in the drug delivery systems and compositions of the present invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of one or more of the active drug or therapeutic compounds provided in the drug delivery systems and compositions of the present invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g. Other embodiments provide, amounts of one or more of the active drug or therapeutic compounds provided in the drug delivery systems and compositions of the present invention in the range of 0.0001-10 g, 0.0005-9 g, 0.001-8 g, 0.005-7 g, 0.01-6 g, 0.05-5 g, 0.1-4 g, 0.5-4 g, 1-3 g, or 1-10 g.

The target dose may be administered in a single dose. Alternatively, the target dose may be administered in about or more than about 1, 2, 3, 4, 5, 6, 7, 8, 9, 10, 11, 12, 13, 14, 15, 16, 17, 18, 19, 20, 25, 30, or more doses.

The administration schedule may be repeated according to any prescribed regimen, including any administration schedule described herein or known in the art. The one or more of the active drug or therapeutic compounds provided in the drug delivery systems and compositions of the present invention may be administered in one dose or multiple dosages.

Methods of determining the most effective means and dosage of administration are well known to those of skill in the art and will vary with the particular compositions used, the purpose of the use, the target cells or tissues being contacted, and the subject being treated. Single or multiple administrations (e.g., about or more than about 1, 2, 3, 4, 5, 6, 7, 8, 9, or 10, or 50, more doses) over the course of from 1, 2, 3, 4, 5, 6, 7, 8, 9, or 10, or 50, or more, minutes, hours, days, weeks, months, or even years.

In some particularly preferred embodiments, one dose of the composition is administered every 1-3, 1-7, 1-10, 1-12, 1-14, 1-28, 1-30, or more, days as prescribed by a physician or as otherwise deemed necessary for therapeutic benefit. Administration can be carried out with the dose level and pattern being selected by the treating physician. It is known in the art that due to intersubject variability in compound pharmacokinetics, individualization of dosing regimens is necessary for optimal therapy. Dosing for compositions of the present invention may be found by routine experimentation in light of the instant disclosure and one's skill in the art.

Additionally, it is to be noted that, similar to the approaches described in the fields of medicinal and pharmaceutical chemistry, a suitable pharmaceutical preparation may also include, optionally, in addition to one or more compounds of the present invention, other agents, including, but not limited to, excipients, diluents, extenders, stabilizers, colors, flavors, formulating agents (e.g., gels and thickeners), antioxidants (e.g., ascorbic acid, butylated hydroxyanisole, butylated hydroxytoluene, citric acid, EDTA, phosphoric acid, sodium ascorbate, sodium metabisulfite, tartaric acid, tertiary butyl hydroquinone), preservatives, sterile aqueous solutions, buffers, sugars, and the like, as are generally known and accepted.

In other embodiments, one or more additional small molecule drug and/or biological agents may be preferentially combined in an admixture (or administered concomitantly) with the one or more active drug or therapeutic compounds provided in the drug delivery systems and compositions of the present invention of the present invention to achieve a beneficial, or even synergistic, outcome in the subject.

The compositions of the present invention can be formulated for delivery into the subject's mouth (e.g., by ingestion, buccal and/or sublingual deposit). In other embodiments, the compositions are formulated for injection (e.g., intramuscular, intradermal, intrathecal, intraperitoneal, intra-arterial, and/or subcutaneous, and the like), infusion (e.g., intraosseous and/or intravenous, and the like), irrigation, instillation (e.g., dropwise instillation) and the like. In still further embodiments, are formulated for topical delivery. In certain cases, delivery of the desired formulation is aided by one or more mechanical device(s) such as microneedles and patches, syringes, pumps, catheters, ports, inhalant delivery devices, biolistic delivery devices, and the like.

Modifications and variations of the present invention will be obvious to those skilled in the art from the foregoing description of the invention. Such modifications and variations are intended to come within the scope of the appended claims.

INCORPORATION BY REFERENCE

All U.S. Patent Publications, U.S. Patent Applications, and U.S. Patents are hereby expressly and specifically incorporated by reference in their entireties, specifically, U.S. Pat. Nos. 5,698,664 and 5,914,388.

What is claimed is:

1. A polymeric drug delivery composition comprising polyphosphazene and at least one therapeutic agent,
   wherein said therapeutic agent comprises a chemotherapeutic agent,
   wherein said chemotherapeutic agent comprises Paclitaxel,
   wherein said Paclitaxel is administered at a dose of 1250-1875 mg/m$^2$ body surface area in a patient, and
   wherein said polyphosphazene is represented by formula J below:

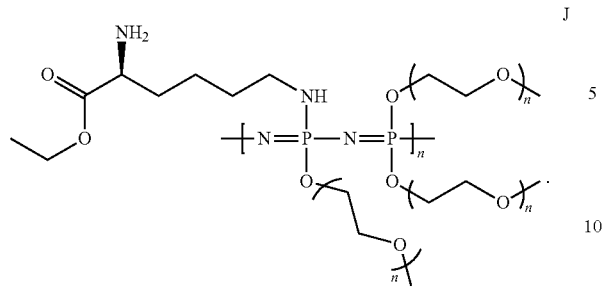

2. The composition of claim 1, wherein said polyphosphazene comprise nanoparticles.

3. The composition of claim 1 for use as a medicament.

4. The composition of claim 1 for use in the treatment of a disease.

5. The use of the composition of claim 4, wherein said disease comprises cancer or a neoproliferative disease.

6. The composition of claim 1, further comprising a kit comprising instructions for administration of said composition to a subject.

7. The kit of claim 6, wherein said subject comprises a human.

* * * * *